United States Patent
Fukazawa et al.

(10) Patent No.: US 10,352,875 B2
(45) Date of Patent: Jul. 16, 2019

(54) INSPECTION APPARATUS, INSPECTION METHOD, EXPOSURE METHOD, AND METHOD FOR MANUFACTURING SEMICONDUCTOR DEVICE

(75) Inventors: Kazuhiko Fukazawa, Kamakura (JP); Yoshihiko Fujimori, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 279 days.

(21) Appl. No.: 13/881,593

(22) PCT Filed: Feb. 10, 2011

(86) PCT No.: PCT/JP2011/000744
§ 371 (c)(1),
(2), (4) Date: Apr. 25, 2013

(87) PCT Pub. No.: WO2012/056601
PCT Pub. Date: May 3, 2012

(65) Prior Publication Data
US 2013/0217154 A1    Aug. 22, 2013

Related U.S. Application Data

(60) Provisional application No. 61/406,708, filed on Oct. 26, 2010.

(30) Foreign Application Priority Data

Dec. 16, 2010 (JP) ................................ 2010-280469
Dec. 27, 2010 (JP) ................................ 2010-289644

(51) Int. Cl.
*G01N 21/95* (2006.01)
*G03F 9/00* (2006.01)
(Continued)

(52) U.S. Cl.
CPC ..... *G01N 21/9501* (2013.01); *G03F 7/70641* (2013.01); *G03F 9/7026* (2013.01); *H01L 22/12* (2013.01); *H01L 2924/0002* (2013.01)

(58) Field of Classification Search
CPC .. G01N 21/9501; G01N 21/956; G01N 21/47; G03F 7/70641
(Continued)

(56) References Cited

U.S. PATENT DOCUMENTS 5,750,294 A    5/1998  Hasegawa et al.
2003/0170552 A1    9/2003  Miyashita et al.
(Continued)

FOREIGN PATENT DOCUMENTS

CN    101490638 A    7/2009
JP    11-274048    10/1999
(Continued)

OTHER PUBLICATIONS

English-language International Search Report from Japanese Patent Office for International Application No. PCT/JP2011/000744, dated May 17, 2011.
(Continued)

*Primary Examiner* — Tri T Ton
*Assistant Examiner* — Rebecca C Bryant
(74) *Attorney, Agent, or Firm* — Finnegan, Henderson, Farabow, Garrett & Dunner, LLP

(57) ABSTRACT

A surface inspection apparatus (1) has a stage (5) for supporting a wafer (10) on which predetermined patterns have been formed by exposure using an exposure device (100); an illumination system (20) for irradiating an illuminating light on the surface of the wafer (10) supported by the stage (5); an imaging device (35) for detecting light from the surface of the wafer (10) on which illuminating light has been irradiated, and outputting a detection signal; and an (Continued)

image processing unit (40) for determining the focus state during exposure, on the basis of the detection signal sent from the imaging device (35).

33 Claims, 27 Drawing Sheets

(51) Int. Cl.
*G03F 7/20* (2006.01)
*H01L 21/66* (2006.01)

(58) Field of Classification Search
USPC ...................................................... 356/237.5
See application file for complete search history.

(56) References Cited

U.S. PATENT DOCUMENTS

| | | |
|---|---|---|
| 2005/0185174 A1 | 8/2005 | Laan et al. |
| 2006/0098189 A1 | 5/2006 | Oomori et al. |
| 2006/0292460 A1 | 12/2006 | Sato et al. |
| 2007/0222979 A1 | 9/2007 | Van Der Laan et al. |
| 2008/0259353 A1 | 10/2008 | Miyashita |
| 2009/0147247 A1 | 6/2009 | Endo et al. |
| 2012/0099120 A1 | 4/2012 | Okamoto |

FOREIGN PATENT DOCUMENTS

| | | |
|---|---|---|
| JP | 2006-135211 | 5/2006 |
| JP | 2007-523488 | 8/2007 |
| JP | 2011-40433 | 2/2011 |
| JP | 2011-40434 | 2/2011 |
| WO | WO 2011/001678 A1 | 1/2011 |
| WO | WO 2008/132799 A1 | 11/2011 |

OTHER PUBLICATIONS

English-language translation of Notification of Reasons for Rejection from the Japanese Patent Office in counterpart Japanese Patent Application No. 2012-540642, dispatched Jul. 18, 2014 (7 pages).
Office Action issued in Taiwanese Application No. 100104531, dated Jun. 24, 2015 (8 pages).
Office Action issued in Japanese Patent Application No. 2012-540642 dated Feb. 20, 2015.
Office Action from the counterpart Taiwan Patent Application No. 100104531.
Office Action issued in Chinese Patent Application No. 2011800518532, dated Mar. 18, 2015.
Notice of Preliminary Rejection issued by Korean Intellectual Property Office in Korean Patent Application No. 10-2013-7013401 dated Jan. 12, 2017, and English translation thereof.
International Preliminary Report on Patentability and Written Opinion of the International Searching Authority issued by the International Bureau of WIPO in International Application No. PCT/JP2011/000744, dated May 23, 2015.
Office Action issued in Taiwanese Application No. 100104531, dated Jan. 26, 2016 (8 pages).

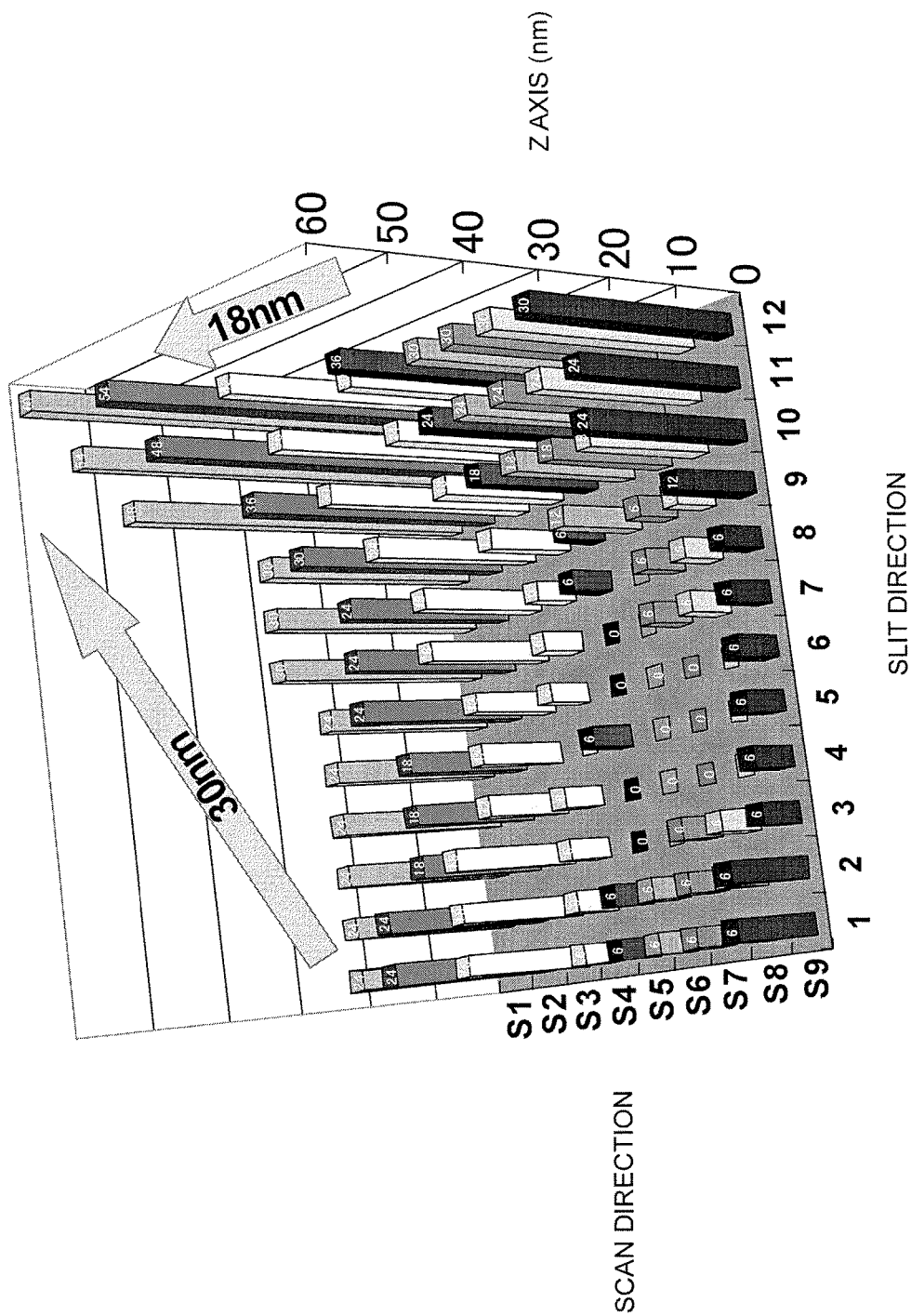

INSPECTION APPARATUS, INSPECTION METHOD, EXPOSURE METHOD, AND METHOD FOR MANUFACTURING SEMICONDUCTOR DEVICE

CROSS REFERENCE TO RELATED APPLICATIONS

This application is a national phase application based on PCT/JP2011/000744, filed Feb. 10, 2011, which claims the benefit of U.S. Provisional Application No. 61/406,708, filed Oct. 26, 2010, and claims the priority of Japanese Patent Application Nos. 2010-280469, filed Dec. 16, 2010, and 2010-289644, filed Dec. 27, 2010, the contents of all of which are incorporated herein by reference.

TECHNICAL FIELD

The present invention relates to an inspection method and an inspection apparatus for inspecting the surface of a substrate on which a predetermined pattern has been formed by exposure, and also relates to an exposure method for exposing a predetermined pattern on the surface of a substrate, and a method for manufacturing a semiconductor device fabricated by the exposure method.

TECHNICAL BACKGROUND

A step-and-scan exposure device moves a stage holding a reticle (i.e., a mask substrate on which a semiconductor pattern has been formed) and a stage holding a wafer (i.e., a wafer on which a semiconductor pattern would be formed) in a relative fashion and scans a distance equal to a single shot while irradiating light in the form of a slit via a mask and projection lens to thereby expose a single shot (a predetermined range) on the semiconductor wafer. In this process, the size of the exposure shot is determined by the long side of the slit (light) and the relative scan distance of the reticle stage. Therefore, the exposure shot can be increased. The exposure shot is also referred as an exposure field.

In such an exposure device, it is very Important to manage focus (a focus state of the pattern on the wafer surface). In view of this fact, the state of focus on the wafer surface in the exposure device is monitored (as used herein, the term focus management is not limited to defects produced by defocusing (non-focus), but also refers to the management of variations in the focus state within a shot or on the entire wafer surface, and variations in the dose (exposure) state). Measurement of the focus state of an exposure device includes measurement of the distribution of the focus state within an exposure shot and measurement of the distribution of the focus state of the entire surface of a wafer. Hereinafter, the former shall be referred to as the image plane or image plane measurement, and the latter shall be referred to as focus monitor or focus monitor measurement. The focus state is expressed as a numerical value that represents the extent to which the focus after exposure is displaced from the best focus or a reference state of focus. A known method for measuring the focus state of an exposure device is to expose and develop a test pattern using, e.g., a dedicated mask substrate, and measure the focus offset distance from the positional displacement of the resulting test pattern.

However, when the focus state of an exposure device is to be measured using such a method, time is required to perform the work to produce the conditions of the parameters required for measurement, and a considerable amount of time is also spent for measurement because the measurement is essentially a point by point measurement. Also, there are limitations on types of patterns and the illumination conditions of the exposure device, and the focus state can only be measured using patterns that are different from those used in actual devices.

Furthermore, in such an exposure device, the height of the mask substrate is adjusted in accordance with the height of the wafer stage in order to match the focus of the projection lens (focusing). However, the focus cannot be matched by a mere primary adjustment of the height of the mask substrate in the case that the image plane (of the pattern) is tilted by the projection lens or the like. In view of the above, such an exposure device measures the optimal focus conditions prior to wafer exposure. A known method for determining the optimal focus conditions is to, e.g., expose and develop a pattern for measurement while the focus is varied for each area smaller than a single slit, and determine conditions that will achieve the best focus on the basis of a regular reflectance image of the resulting pattern (e.g., see patent document 1). In this case, the regular reflectance image of the pattern is magnified and observed using a microscope and imaging elements, the conditions in which the contrast between the resist pattern (line) and space is maximum are determined to be the conditions of best focus.

However, in the case that the optimal focus conditions are determined using such a method, there are cases in which the required precision cannot be satisfied in that the thickness of the resist (resist film reduction) varies due to variation in exposure energy, and pattern loss and other impacts readily occur due to excessive defocus. Control errors end up being included and precision is reduced during image plane measurement within a shot because the focus is varied and exposure is carried out for each area smaller than a single shot. The semiconductor pattern image formed by the photo resist on the wafer may also tilt in a relative manner due to errors that occur during reticle-stage or wafer-stage scanning, and compensation for such errors cannot be made.

PRIOR ARTS LIST

Patent Document

Patent Document 1: Specification of US Laid-open Patent Application No. 2008/0207499(A1)

SUMMARY OF THE INVENTION

Problems to be Solved by the Invention

As described above, there is a need for a method for measuring exposure states (focus state, dose state) during exposure with good precision in a short period of time.

The present invention was developed in view of the problems described above, and an object of the present invention is to provide an apparatus and method capable of measuring exposure states during exposure with good precision in a short period of time.

Means to Solve the Problems

The inspection apparatus of the present invention for achieving the abovementioned objects comprises: an illumination unit for irradiating an illuminating light on a plurality of patterns on a substrate, the patterns being fabricated by repeated exposure within a predetermined range; a detection unit for detecting in a lump the light from the patterns of the predetermined range on the substrate on which the illuminating light has been irradiated; and a computation unit for determining, on the basis of detection results produced by the detection unit, a state of exposure when the patterns were exposed.

In the inspection apparatus described above, it is preferred that the computation unit compute as the exposure state the exposure amount and/or the focus state in effect when the patterns were exposed.

It is preferred that the inspection apparatus described above further comprise a controller for controlling the illumination unit and the detection unit, and that the controller control the illumination unit and/or the detection unit so that when one of the focus state and the exposure amount is computed as the exposure state, the impact from the other will be lower.

In the inspection apparatus described above, it is preferred that the detection unit detect diffracted light from the patterns.

In the inspection apparatus described above, it is preferred that the detection unit detect diffracted light of a fourth order or greater.

In the inspection apparatus described above, it is preferred that the detection unit detect a predetermined polarized light component in light reflected from the patterns.

It is preferred that the inspection apparatus described above further comprise a storage unit for storing detection results for a plurality of patterns exposed in a plurality of different exposure states, and an input unit capable of communication, the computation unit determining the exposure state in effect when the patterns were exposed on the basis of the stored detection results.

In the inspection apparatus described above, it is preferred that the storage unit be capable of storing a plurality of different exposure states and the detection results of patterns exposed in the exposure states; and that the computation unit determine the exposure state in effect when patterns to be inspected were exposed, on the basis of the stored detection results and the detection results for the patterns to be inspected.

In the inspection apparatus described above, it is preferred that the storage unit be capable of storing an exposure state curve showing the relationship between the plurality of different exposure states and the detection results for the patterns exposed in the exposure states; and that the computation unit determine the exposure state in effect when patterns to be inspected were exposed, on the basis of points of inflection of the exposure state curve.

In the inspection apparatus described above, it is preferred that the storage unit be capable of storing an exposure state curve showing the relationship between the plurality of different exposure states and the detection results for the patterns exposed in the exposure states; and that the computation unit determine the exposure state in effect when the patterns to be inspected were exposed, by fitting of the detection results for the patterns to be inspected and the exposure state curve.

In the inspection apparatus described above, it is preferred that the detection unit detect light from the patterns over a plurality of cycles, and that the computation unit determine the exposure state on the basis of an integral signal obtained by integrating the results of the plurality of detections.

It is preferred that the inspection apparatus described above further comprise a modification unit for modifying the relative position between the substrate and the detection unit, and/or the relative position between the substrate and the illumination unit, the computation unit determining the exposure state in effect when patterns to be inspected were exposed, on the basis of the detection results before and after modification of the relative position.

In the inspection apparatus described above, it is preferred that the computation unit determine the exposure state on the basis of the average of the detection results of a plurality of the relative positions.

In the inspection apparatus described above, it is preferred that the illumination unit illuminate in a lump using parallel luminous flux the entire surface on which a substrate pattern has been formed; and the detection unit detect in a lump the light from the pattern on the surface.

It is preferred that the inspection apparatus described above further comprise an output unit for outputting the exposure state determined by the computation unit, the exposure state being sent so as to be capable of being feed back to the exposure device that performed the exposure.

The inspection method of the present invention comprises the steps of: irradiating an illuminating light on a plurality of patterns on a substrate, the patterns being fabricated by repeated exposure within a predetermined range; detecting in a lump the light from the patterns of the predetermined range of the substrate on which the illuminating light has been irradiated; and determining, on the basis of the detection results, an exposure state in effect when the patterns were exposed.

In the inspection method described above, it is preferred that the exposure state and/or the focus state in effect when the patterns were exposed be determined as the exposure state.

In the inspection method described above, it is preferred that the illumination and/or the detection be controlled so that when the focus state and/or the exposure state is to be determined, the impact from the other will be lower.

In the inspection method described above, it is preferred that diffracted light from the patterns be detected.

In the inspection method described above, it is preferred that a predetermined polarized light component of light from the patterns be detected.

In the inspection method described above, it is preferred that the exposure state in effect when a plurality of patterns was exposed is determined on the basis of the detection results for the patterns exposed in a plurality of different exposure states.

In the inspection method described above, it is preferred to determine the exposure state when patterns to be inspected on the basis of the relationship between the detection results of a plurality of patterns exposed in a plurality of different exposure states and the exposure state in effect when the patterns were exposed.

In the inspection method described above, it is preferred that the exposure state in effect when patterns to be inspected were exposed be determined on the basis of points of inflection of an exposure state curve, using the exposure state curve as the relationship between the detection results of a plurality of patterns exposed in a plurality of different exposure states and the exposure state in effect when the patterns were exposed.

In the inspection method described above, it is preferred that the exposure state in effect when the patterns to be inspected were exposed be obtained on the basis of fitting of the detection results for the patterns to be inspected and the exposure state curve, using the exposure state curve as the relationship between the detection results of a plurality of patterns exposed in a plurality of different exposure states and the exposure states in which the patterns were exposed.

In the inspection method described above, it is preferred that light from the patterns be detected over a plurality of cycles, and the results of the plurality of detections be integrated to determine the exposure state in effect when the patterns to be inspected were exposed.

In the inspection method described above, it is preferred that the state of irradiation of the illuminating light and/or the state of detection of light from the patterns be modified, and the exposure state in effect when the patterns to be inspected were exposed be determined on the basis of the detection results produced before and after modification.

In the inspection method described above, it is preferred that the exposure state be obtained on the basis of the average of the detection results produced before and after modification.

In the inspection method described above, it is preferred that the entire surface on which the patterns were formed be illuminated in a lump, and the light from the patterns on the entire surface be detected in a lump.

In the inspection method described above, it is preferred that exposure state in effect when the patterns to be inspected were exposed be determined and used as information that can be feed back to the exposure device that exposed the patterns.

The exposure method according to the present invention decides exposure conditions on the basis of information that can be feed back, the information being obtained in accordance with the inspection method according to the present invention.

The method for manufacturing a semiconductor device of the present invention carries out fabrication in accordance with the exposure method according to the present invention.

Advantageous Effects of the Invention

In accordance with the present invention, the exposure state during exposure can be measured with good precision in a short period of time.

BRIEF DESCRIPTION OF THE DRAWINGS

FIG. 10 is a view showing the distribution of the focus offset amount within a shot;

DESCRIPTION OF THE EMBODIMENTS

Figure 1:
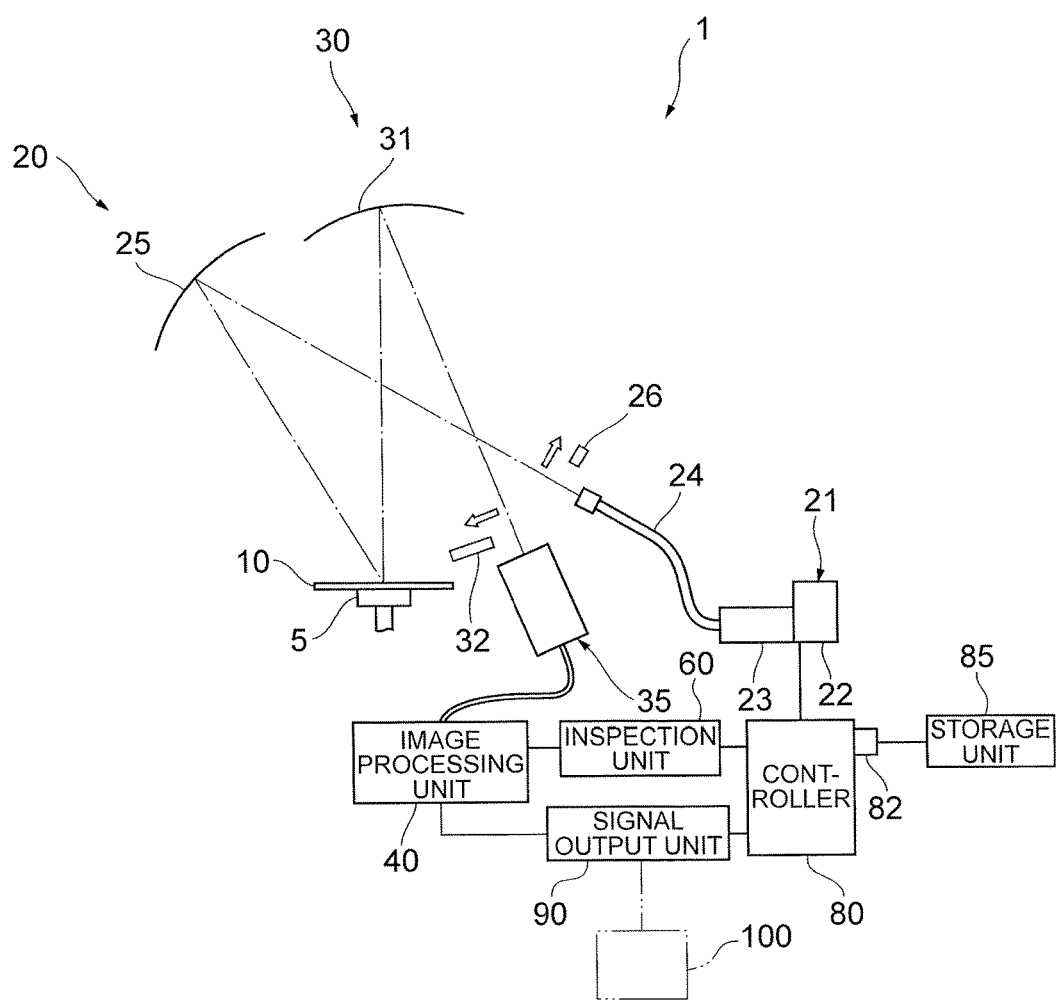
FIG. 1 is a view showing the overall configuration of the surface inspection apparatus.

Preferred embodiments of the present invention will be described below with reference to the drawings. FIG. 1 shows the surface inspection apparatus of the first embodiment; the apparatus inspecting the surface of a semiconductor wafer 10 (hereinafter referred to as wafer 10), which is a semiconductor substrate. The surface inspection apparatus 1 of the first embodiment comprises a stage 5 for supporting a substantially disc-shaped wafer 10, as shown in FIG. 1, and the wafer 10 transported by a transport device (not shown) is mounted on the stage 5, and secured thereto and held by vacuum chucking. The stage 5 rotatably supports the wafer 10 (rotation within the surface of the wafer 10) about the axis of rotational symmetry of the wafer 10 (the center axis of the stage 5). The stage 5 is capable of tilting (inclining) the wafer 10 about the axis that passes through the surface of the wafer 10, and is also capable of adjusting the incident angle of the illuminating light.

The surface inspection apparatus 1 is furthermore composed of an illumination system 20 for irradiating an illuminating light as parallel light onto the surface of the wafer 10 supported on the stage 5, a light-receiving system 30 for collecting reflected light, diffracted light, and the like from the wafer 10 when illuminating light is received, an imaging device 35 for receiving light collected by the light-receiving system 30 and detecting an image on the surface of the wafer 10, an image processing unit 40, an inspection unit 60, a controller 80, and a storage unit 85. The controller 80 is provided with a communication port 82 for transferring (communicating) storage information to and from the storage unit 85. The illumination system 20 has an illumination unit 21 for emitting illuminating light, and an illumination-side concave mirror 25 for reflecting toward the surface of the wafer 10 the illuminating light emitted from the illumination unit 21. The illumination unit 21 has: a metal halide lamp, a mercury lamp, or other light source unit 22; a dimming unit 23 for extracting light having a predetermined wavelength in the light from the light source unit 22 and adjusting the intensity by a command from the controller 80; and a light-guide fiber 24 for directing light from the dimming unit 23 as illuminating light to the illumination-side concave mirror 25.

The light from the light source unit 22 passes through the dimming unit 23 (comprising a neutral density filter and a turret plate having a plurality of band-pass filters of differing transmission wavelengths; the intensity and wavelength of the illuminating light are controlled on the basis of a command from the controller 80), illuminating light with a predetermined intensity having a predetermined wavelength (e.g., a wavelength of 248 nm) is emitted from the light-guide fiber 24 toward the illumination-side concave mirror 25, and since the emission unit of the light-guide fiber 24 is disposed on the focus plane of the illumination-side concave mirror 25, the illuminating light emitted from the light-guide fiber 24 toward the illumination-side concave mirror 25 is formed into parallel luminous flux by the illumination-side concave mirror 25 and is irradiated onto the surface of the wafer 10 held on the stage 5. The relationship between the incident angle and the exit angle of the illuminating light with respect to the wafer 10 can be adjusted by tilting (inclining) the stage 5 by a command from the controller 80 and varying the placement angle of the wafer 10.

Figure 2:
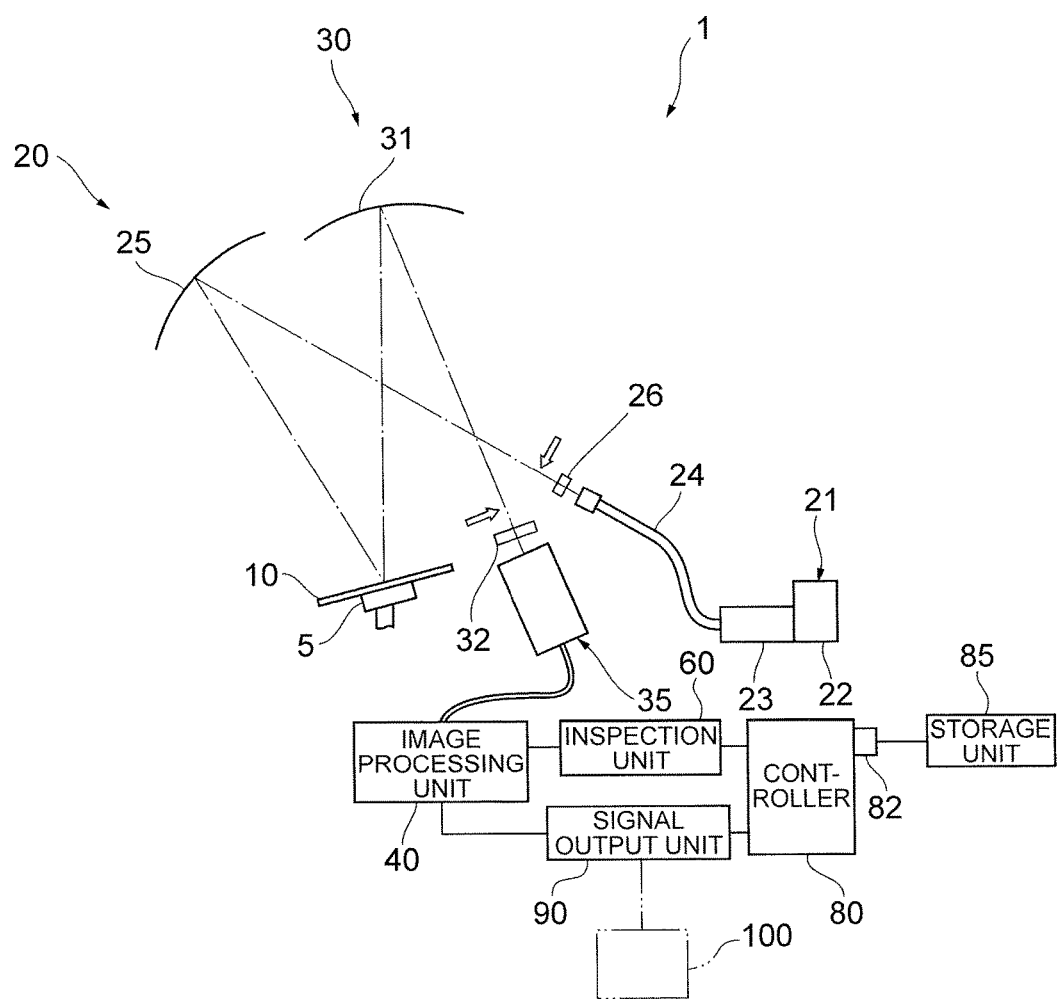
FIG. 2 is a view showing the state in which a polarizing filter has been inserted into the optical path of the surface inspection apparatus.

An illumination-side polarizing filter 26 is disposed so as to be capable of being inserted into the optical path between the light-guide fiber 24 and the illumination-side concave mirror 25 by an illumination-side polarizing filter drive unit (not shown) on the basis of a command from the controller 80, inspection is carried out using diffracted light in a state in which the illumination-side polarizing filter 26 has been removed from the optical path (for convenience, hereinafter referred to as diffraction inspection), as shown in FIG. 1, and inspection is carried out using polarized light (variation in the state of polarization produced by structural birefringence) in a state in which the illumination-side polarizing filter 26 has been inserted into the optical path (for convenience, hereinafter referred to as PER inspection), as shown in FIG. 2 (the details of the illumination-side polarizing filter 26 are described later). It is also possible to dispose the illumination-side polarizing filter 26 in the optical path so that the illuminating light becomes s polarized light and then perform diffraction inspection. With diffraction inspection using s polarized light, there is little impact from the base layer and it is possible to detect the state of the uppermost layer.

The light (diffracted light or reflected light) emitted from the surface of the wafer 10 is collected by the light-receiving system 30. The light-receiving system 30 is mainly composed of a light-receiving-side concave mirror 31 arranged facing the stage 5, the emitted light (diffracted light or reflected light) collected by the light-receiving-side concave mirror 31 arrives on the imaging surface of the imaging device 35, and the image of the wafer 10 is formed.

A light-receiving-side polarizing filter 32 is disposed so as to be capable of being inserted into the optical path between the light-receiving-side concave mirror 31 and the imaging device 35 by an light-receiving-side polarizing filter drive unit (not shown) on the basis of a command from the controller 80, diffraction inspection is carried out in a state in which the light-receiving-side polarizing filter 32 has been removed from the optical path, as shown in FIG. 1, and PER inspection is carried out using polarized light in a state in which the light-receiving-side polarizing filter 32 has been inserted into the optical path, as shown in FIG. 2 (the details of the light-receiving-side polarizing filter 32 are described later).

The imaging device 35 photoelectrically converts the image of the surface of the wafer 10 formed on the imaging plane to generate an image signal and outputs the image signal to the image processing unit 40. The image processing unit 40 generates a digital image of the wafer 10 by command of the controller 80 on the basis of the image signal of the wafer 10 received from the imaging device 35. Image data of a non-defective wafer is stored in advance in the internal memory (not shown) of the image processing unit 40, and when an image (digital image) of the wafer 10 is generated, the image processing unit 40 compares the image data of the wafer 10 and the image data of a non-defective wafer using the inspection unit 60, and inspects for the existence of defects (abnormalities) in the surface of the wafer 10. The inspection results produced by the image processing unit 40 and the inspection unit 60, and the image of the inspected wafer 10 are sent and displayed by an image display device (not shown). The image processing unit 40 is capable of determining (later described in detail) the focus state (e.g., the tilt of the image plane of the patterns projected and exposed by an exposure device 100, the state of variation of the focus of the exposure device 100), and the dose state (e.g., the state of variation of the amount of exposure energy within a shot or between shots of a pattern projected and exposed by the exposure device 100) during exposure using an image of the wafer.

Figure 3:
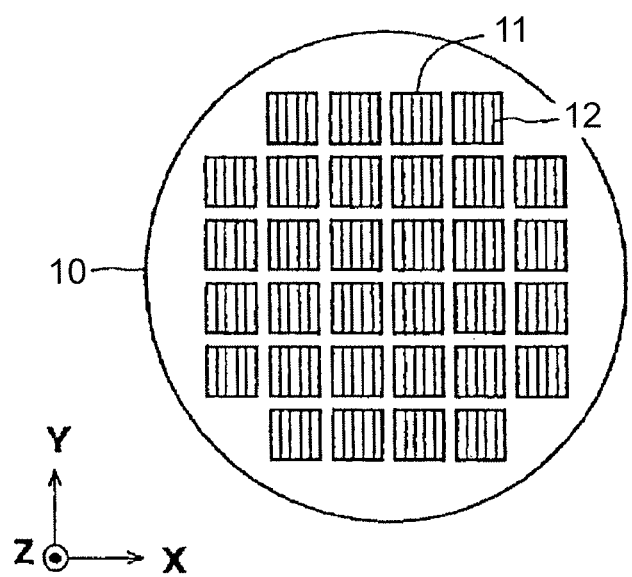
FIG. 3 is a view showing the external appearance of the surface of a semiconductor wafer.

The wafer 10 has a predetermined pattern projected and exposed by the exposure device 100 on a resist film on the uppermost layer, is developed by a developing device (not shown), and is thereafter transported on the stage 5 from a wafer cassette (not shown) or the developing device by a transport device (not shown). The wafer 10 is transported on the stage 5 in a state in which alignment is carried out using the pattern or external periphery (a notch, orientation flat, or the like) of the wafer 10 as a reference. A plurality of chip areas 11 is arrayed longitudinally and laterally (in the XY direction in FIG. 3) on the surface of the wafer 10, as shown in FIG. 3, and a line pattern, a hole pattern, and other repeating patterns 12 are formed as a semiconductor pattern in each of the chip areas 11. A plurality of chip areas is often included in a single exposure shot, but a single chip per shot is used in order to facilitate understanding in FIG. 3. Although a detailed drawing of the exposure device 100 is omitted, the device is the aforedescribed step-and-scan exposure device, which is electrically connected via cables and the like to a signal output unit 90 of the surface inspection apparatus 1 of the present embodiment, and is configured so that exposure control can be adjusted on the basis of data (signals) from the surface inspection apparatus 1.

The controller 80 reads, via the communication port 82, recipe information (inspection conditions, procedures, and the like) stored in the storage unit 85 to perform diffraction inspection of the surface of the wafer 10 using the surface inspection apparatus 1 configured in the manner described above (the procedure for detecting the focus state is described below, and the procedure for detecting the dose state is later described.), and carries out the following process. First, the illumination-side polarizing filter 26 and the light-receiving-side polarizing filter 32 are removed from the optical path, as shown in FIG. 1, and the wafer 10 is transported on the stage 5 by the transport device (not shown). The position information of the patterns formed on the surface of the wafer 10 is acquired by an alignment mechanism (not shown) during transport, and the wafer 10 can be mounted in a predetermined position and predetermined direction on the stage 5.

The stage 5 is subsequently rotated so that the repeating direction of the patterns and the illumination direction on the surface of the wafer 10 match (orthogonal to the line in the case that of a line pattern), and settings are made so as to satisfy the following formula (1) on the basis of Huygens principle, where P is the pitch of the patterns, λ is the wavelength of the illuminating light to be irradiated onto the surface of the wafer 10, θ1 is the incident angle of the illuminating light, and θ2 is the exit angle of the diffracted light of the $n^{th}$ order.

$$P = n \times \lambda / \{\sin(\theta 1) - \sin(\theta 2)\} \qquad (1)$$

Next, the illuminating light is irradiated on the surface of the wafer 10. When the illuminating light is irradiated on the surface of the wafer 10 under such conditions, the light from the light source unit 22 in the illumination unit 21 passes through the dimming unit 23, illuminating light having a predetermined wavelength (e.g., a wavelength of 248 nm) and a predetermined intensity is emitted from the light-guide fiber 24 toward the illumination-side concave mirror 25, and the illuminating light reflected by the illumination-side concave mirror 25 is formed into parallel luminous flux and irradiated on the surface of the wafer 10. The diffracted light diffracted at the surface of the wafer 10 is collected by the light-receiving-side concave mirror 31 and arrives on the imaging plane of the imaging device 35, and an image (a diffraction image) of the wafer 10 is formed.

The imaging device 35 photoelectrically converts the image of the surface of the wafer 10 formed on the imaging plane to generate an image signal and outputs an image signal to the image processing unit 40. The image processing unit 40 generates a digital image of the wafer 10 on the basis of the image signal of the wafer 10 received from the imaging device 35. The image processing unit 40 generates an image (digital image) of the wafer 10, then compares the image data of the wafer 10 and the image data of a non-defective wafer, and inspects for the existence of defects (abnormalities) in the surface of the wafer 10. The inspection results produced by the image processing unit 40 and the image of the inspected wafer 10 are sent and displayed by an image display device (not shown).

The image processing unit 40 is capable of determining a focus curve (a curve showing the relationship between the focus offset amount and the intensity of the diffracted light) produced by the diffracted light, using the image of the wafer exposed and developed under conditions in which the focus offset amount of the exposure device 100 has been varied for each shot. Using the focus curve to determine a focus offset amount in which the signal intensity of the diffracted light is greatest (maximum) for each very small area within a single shot makes it possible to determine an image plane of the patterns projected and exposed by the exposure device 100 (the distribution of the focus state within an exposure shot). As used herein, the term signal intensity is the signal intensity that corresponds to the intensity of the light detected by the imaging elements of the imaging device 35, and is determined by the intensity of the illuminating light, the diffraction efficiency of the patterns, the sensitivity of the imaging device, and other factors. In the present embodiment, the signal intensity is observed as image brightness, and these two terms essentially refer to the same concept. The inventors of the present application found that the best focus, in the case of diffracted light, is the focus offset amount in which the signal intensity is maximum when the line-and-space duty ratio is a single line for 10 or more spaces. The term "maximum" refers to the maximum point within the measured range (near best focus) of the focus, among a maximum of three extrema (upward or downward peaks) of a fourth order function.

Figure 6:
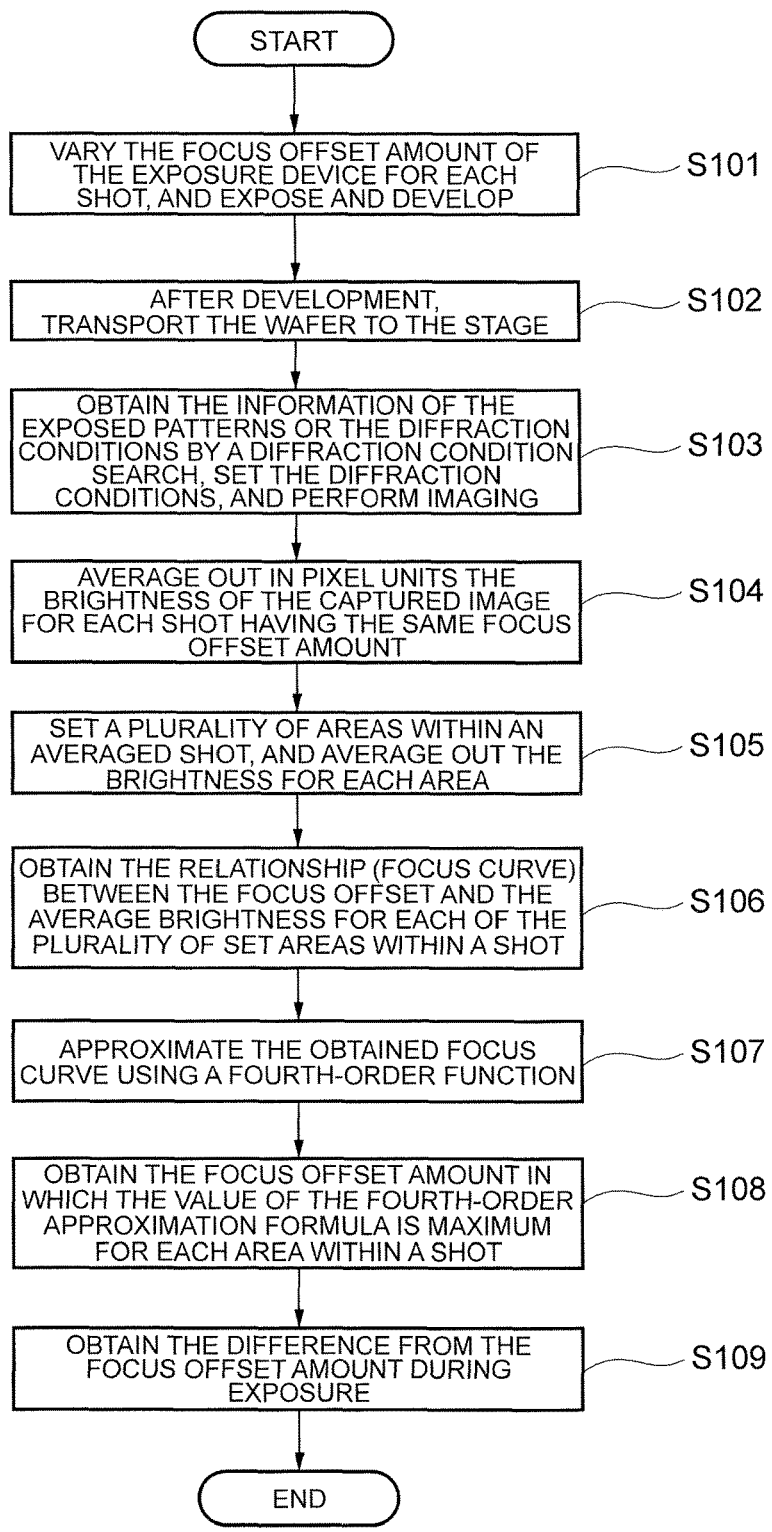
FIG. 6 is a flowchart showing the method for determining the tilt of the image plane of the exposure device.

In view of the above, a method for determining the tilt of the image plane of the patterns projected and exposed by the exposure device 100 will be described with reference to the flowchart shown in FIG. 6. First, a wafer is fabricated having the focus offset amount of the exposure device 100 varied for each shot to form a repeating pattern (step S101). At this point, the focus offset amount is varied for each exposure shot, a plurality of shots having the same focus offset amount is set and these are arranged in a random fashion. Hereinafter, such a wafer will be referred to as a condition-varied wafer 10a (see FIGS. 7 and 8).

In this case, the reason for arranging shots having the same focus offset amount in a random fashion is to cancel, e.g., the difference in resist conditions generated between the center side and the external peripheral side of the wafer, the so-called crosswise difference during scan exposure, and other impacts. The resist film (photoresist) formed on the wafer is often formed by spin coating. The solvent components volatilize as the resist formula is spread by spinning, the viscosity increases, the film tends to increase in thickness, and differences in the resist conditions are generated between the center side and the external peripheral side of the wafer. Also, in the case that the scan direction is the X direction, the so-called crosswise difference is the difference between in case of exposing when the reticle is in the X+ direction (the wafer moves in the X− direction) and in case of exposing when the reticle is moved in the X− direction (the wafer moves in the X+ direction)

Figure 7:
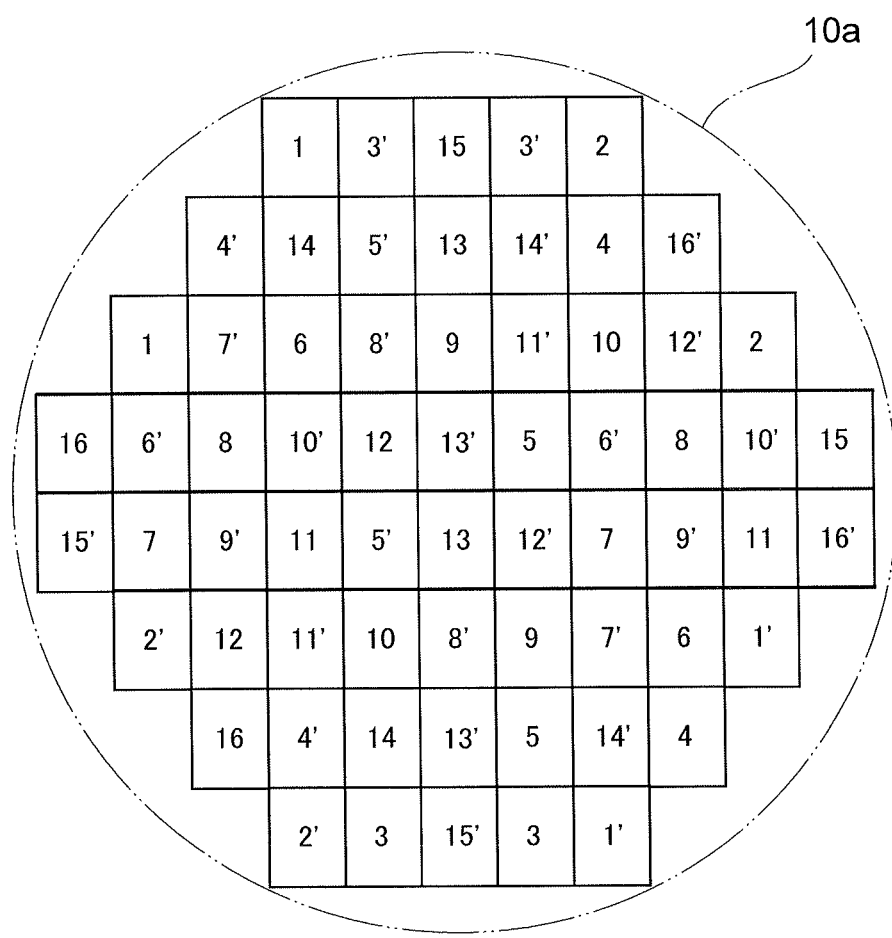
FIG. 7 is a table showing the focus offset amount set by a condition-varied wafer.

The condition-varied wafer 10a of the present embodiment has focus offset amounts varied in 16 steps of 25-nm increments between −175 nm to +200 nm, as shown in FIG. 7. Each shot in FIG. 7 has a number (1 to 16) that indicates a step in the focus offset amounts varied in 25-nm intervals, and has a """ mark in the case that the step is the same but the scan direction is in the opposite direction. For example, shots having a focus offset amount expressed by the number 12 are provided in four locations in which the exposure carried out at the same focus offset amount are a shot with the reticle movement being in the X+ direction on the center side, a shot with the reticle movement being in the X+ direction on the external peripheral side, a shot with the reticle movement being in the X− direction on the center side, and a shot with the reticle movement being in the X− direction on the external peripheral side. In another example, shots having a focus offset amount expressed by the number 15 are provided in four locations in which the exposure carried out at the same focus offset amount are two shots with the reticle movement being in the X+ direction on the external peripheral side, and two shots with the reticle movement being in the X− direction on the external peripheral side, using the center of the condition-varied wafer 10a as a symmetrical axis. In the present embodiment, the focus offset amounts are divided in this manner into 16 steps with four shots per focus offset amount for a total of 64 shots, and these shots are arranged in a random fashion to produce a condition-varied wafer 10a.

A plurality of condition-varied wafers may be fabricated to determine a focus curve. In such a case, the shot arrangement for each focus offset amount of the condition-varied wafers is preferably set so that an impact other than the focus offset is cancelled out.

When the condition-varied wafer 10a is fabricated, the condition-varied wafer 10a is transported on the stage 5 (step S102) in the same manner as diffraction inspection. Next, illuminating light is irradiated onto the surface of the condition-varied wafer 10a in the same manner as diffraction inspection. The imaging device 35 photoelectrically converts the diffraction image of the condition-varied wafer 10a to generate an image signal, and outputs an image signal to the image processing unit 40 (step S103). At this point, the diffraction conditions are determined for the condition-varied wafer 10a using the pitch information of the exposed pattern or a diffraction condition search, and settings are made in the same manner as diffraction inspection so that diffracted light can be obtained. A diffraction condition search refers to a function for varying the tilt angle of the stage 5 in a stepwise fashion within an angle range that excludes specular reflectance to acquire an image at each of the tilt angles, and determining the tilt angle at which the image brightens, i.e., the tilt angle at which diffracted light is obtained. The azimuth angle (the orientation with respect to illumination direction of the illuminating light of the exposed pattern) of the condition-varied wafer 10a is arranged so that the illumination direction matches the repeating direction of the exposed pattern (the direction orthogonal to the line in the case of a line-and-space pattern).

Figure 8:
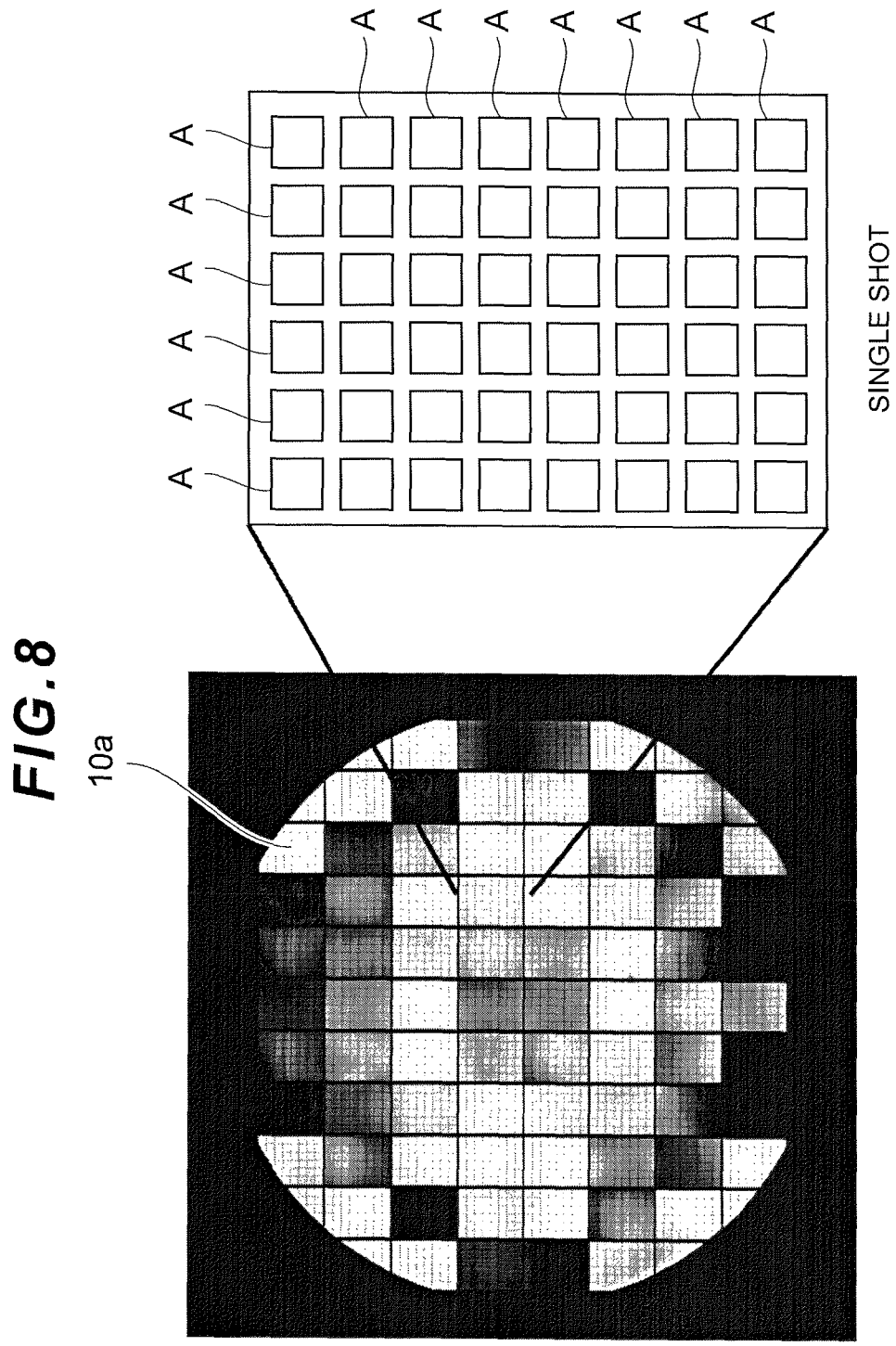
FIG. 8 is a view showing an example of the condition-varied wafer.

Next, the image processing unit 40 generates a digital image of the condition-varied wafer 10a on the basis of the image signal of the condition-varied wafer 10a received from the imaging device 35, and averages out the signal intensity (brightness) in pixel units (the pixels of the corresponding portions of each shot) for each shot for which the focus offset amount is the same (step S104). The portions determined to be defective in the diffraction inspection are excluded from the above-described averaging. The image processing unit 40 then obtains the average value (for convenience, hereinafter referred to as average brightness) of the signal intensity in a plurality of set areas A (areas enclosed by small rectangles) set within a shot for all of the shots obtained by averaging (mutually different focus offset amounts), as shown in FIG. 8 (step S105). In the processing to this point, the average brightness is obtained for each of a plurality of set areas A within an exposure shot, where the focus offset has been varied in 16 steps of 25-nm increments between −175 nm to +200 nm.

Figure 9:
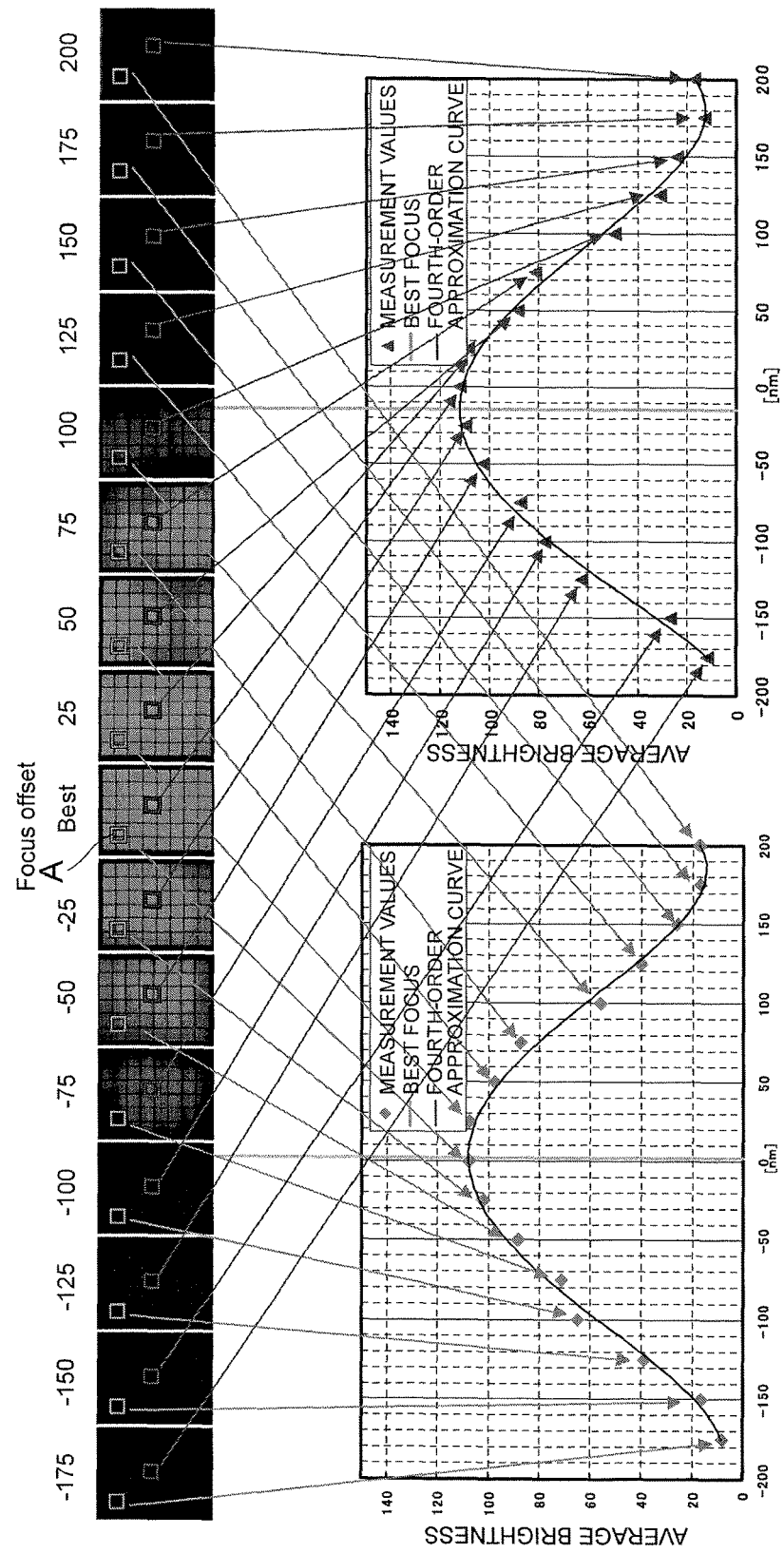
FIG. 9 is a view showing an example of a focus curve.
Figure 13:
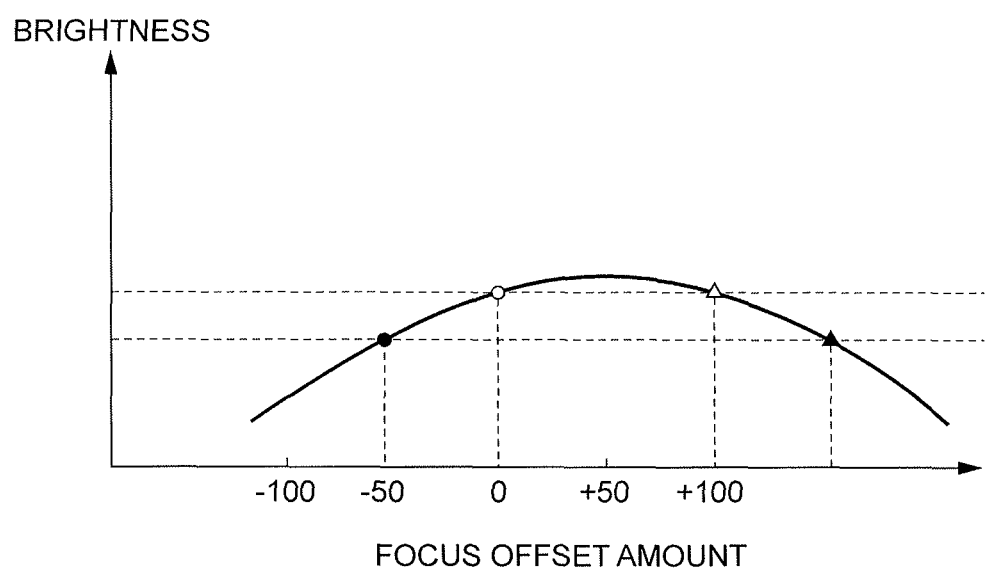
FIG. 13 is a view showing an example of a focus curve.
Figure 14:
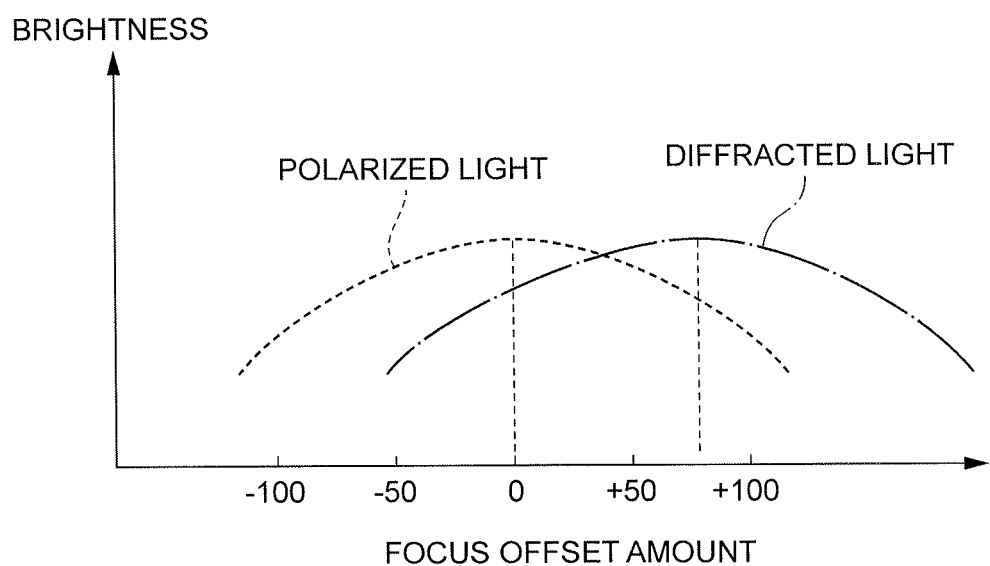
FIG. 14 is a view showing an example of a focus curve.

The image processing unit 40 determines a graph, i.e., a focus curve showing the relationship between the focus offset and the average brightness for each of the set areas A for which the average brightness has been determined (step S106). Examples of a focus curve are shown in FIGS. 9, 13, and 14. Next, the image processing unit 40 determines an approximate curve determined by approximating the focus curve using a function for each of the set areas A (step S107). A fourth-order function (a quartic equation) is preferably used as the function of the approximate curve. Also, the focus curve thus determined in this case shall be referred to as a reference focus curve. The fourth-order function is expressed in the following formula (2).

$$y = ax^4 + bx^3 + cx^2 + dx + e \quad (2)$$

In the formula, x is the focus offset, y is the signal intensity (average brightness), and a, b, c, d, and e are coefficients. The optimal coefficients a, b, c, d, and e for approximating the focus curve is determined using the method of least squares or the like to thereby obtain the approximation function of formula (2).

Next, the image processing unit 40 determines the focus offset amount for which the average brightness on the approximate curve of the focus curve is maximum (step S108). This makes it possible to determine a distribution of the focus offset amounts for which the average brightness of the diffracted light is maximum, as shown in FIG. 10, and the result of calculating the difference between these values and the focus offset setting value during exposure for each of the set areas within an exposure shot is the measured value of the image plane (step S109).

The tilt of the focus (i.e., the amount of slope of the image plane) in the lengthwise direction of the slit (light) exposed by the exposure device 100, and the tilt of the focus in the scan direction between the wafer stage and reticle stage (not shown) of the exposure device 100 are each determined (by approximation) on the basis of the measured value of the image plane. The reason that the image plane can be measured in the manner described above is based on the assumption that the focus offset amount for which the intensity of the diffracted light is maximum is the best focus, but depending on the pattern, there may be a difference between the best focus and the focus offset amount for which the intensity of the diffracted light is maximum. However, even in such a case, the difference between the best focus and the offset amount is constant because the patterns within a shot are each similar, and since the tilt of the image plane is a relative tilt of the value of the set areas of the measured value, the tilt of the image plane can be determined from the measured value of the image plane determined in the manner described above. The results of measuring the image plane determined in this manner are converted to, e.g., image plane curvature, maximum and minimum values, the tilt in the diagonal direction, and other parameters that can be accepted by the exposure device 100, are thereafter sent from the image processing unit 40 to the exposure device 100 via a signal output unit (not shown), and are reflected in the exposure carried out by the exposure device 100. The tilt of the image plane in the present embodiment is the overall tilt of the image plane in relation to the photoresist layer on the wafer as produced by the scan error of the reticle and wafer stages and by the tilt of the image plane of the projected image produced by the projection lens in the exposure device 100.

In this manner, in accordance with the present embodiment, the image processing unit 40 determines the tilt (the tendency of focus displacement within the repeating pattern 12 formed on the wafer 10) of the image plane of the pattern projected and exposed by the exposure device 100, on the basis of the image of the condition-varied wafer 10a exposed by the exposure device 100. Therefore, measurement can be performed on the basis of not only a pattern dedicated for measurement, but also an image of the wafer exposed and developed using a pattern used in production exposure and illumination conditions. At this point, in the present embodiment, each of the patterns exposed while the focus offset amount of the exposure device 100 is varied for each shot can be captured in a lump on the surface of the condition-varied wafer 10a. Accordingly, imaging can be carried out in a short period of time and, when the maximum brightness (intensity) of the diffracted light is determined for each of the set areas A within a shot, the impacts of variations in the thickness of the resist film and the like can be reduced because the average brightness of the set areas A is determined for each shot having a different focus offset amount on the condition-varied wafer 10a. Thus, measurement can be carried out on the basis of an image of exposed shots with a pattern used for production exposure, and furthermore, since the impacts of variations in the thickness of the resist film and the like can be averaged and reduced, a corresponding optical image plane of the exposure device 100 can be measured with good precision.

In the description above, the condition-varied wafer 10a has a plurality of shots having the same focus offset amount, and these shots are arranged in a random fashion, but it is also possible to measure the image plane using a "focus exposure matrix wafer" (FEM wafer), which is generally used for adjusting an exposure device. An FEM wafer is exposed and developed with focus and dose (exposure energy) varied in the form of a matrix, and therefore generally has a single shot with the same focus offset amount and the same dose amount. Therefore, the impacts of variation or the like in the thickness of the resist film cannot be averaged out by averaging. Although measurement precision is slightly inferior as a consequence, the focus curve can be determined using a shot having a constant dose amount and different focus offset amounts to measure the image plane (dose variations can be measured as described below using a shot having a constant focus offset amount and different dose amounts).

The impacts of variations in the thickness of the resist film and the like are unlikely to occur when an image produced by diffracted light generated from the surface of the wafer is captured. Therefore, a corresponding optical image plane of the exposure device 100 can be measured with good precision.

In this case, high-precision measurements are made possible by selecting optimal diffraction conditions for each of various target patterns. In particular, sensitivity with respect to very small variations in focus is high, and high resolution can be achieved.

Regarding the exposure conditions of the exposure device, image plane measurement with few impacts is possible by selecting suitable diffraction conditions against non-uniformities in the illumination system within a shot and non-uniformities produced by lens hazing or the like. In prior art, non-uniformities in contrast produced by non-uniformities and the like in the illumination system within a shot are also factors that reduce precision.

Precision can be further improved by selecting a plurality of diffraction conditions depending on the target pattern, and averaging the relative image plane (the tilt of the image plane) of the exposure device 100 determined in the diffraction conditions. In this case, for example, averaging can be performed with good precision by offsetting each of the image planes determined in each of the diffraction conditions so as to achieve the same focus offset amount using the center position within a shot as a reference. At this point, it is preferred that high-order diffraction conditions and wavelength be selected. For conditions in which a plurality of pattern pitches is present, precision is stably improved when images obtained under different pitch conditions are acquired and analyzed, and conditions that produce a sharp curve in the focus curve are used. Abnormal values are preferably removed when averaging is carried out.

When diffraction conditions are to be selected, it is possible to obtain precision with no impact on the image plane measurement, even when the dose (energy) within a shot is not uniform, by selecting diffraction conditions in which the best focus position substantially does not change regardless of the dose amount. As described in prior art, when the focus offset amount is varied within a smaller area than a single shot, and exposure and measurement are carried out, errors are conventionally generated because the energy distribution within different shots is measured. In order to select diffraction conditions in which the best focus position substantially does not change regardless of the dose amount, it is possible to determine and compare the focus curve for each different dose amount using, e.g., the above-described FEM wafer, and select conditions for which the best focus position is not changed by the dose amount.

Figure 11A:
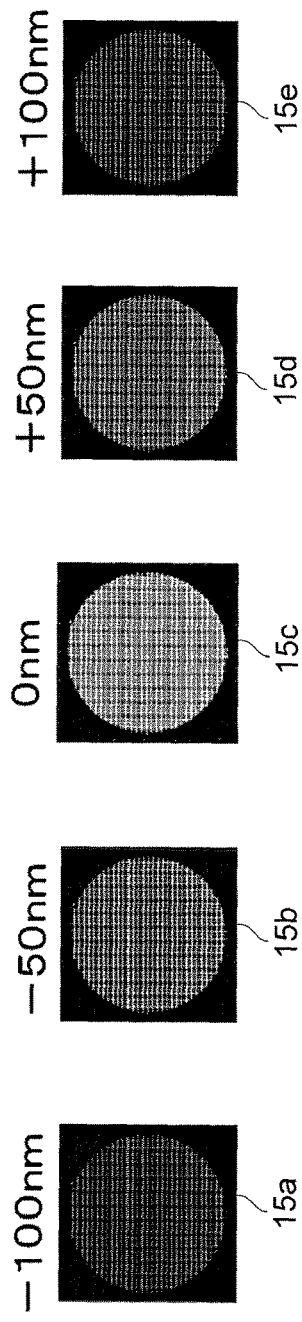
FIG. 11 is a view showing the procedure for determining the focus state during exposure in the sequence of (a) to (b)
Figure 17:
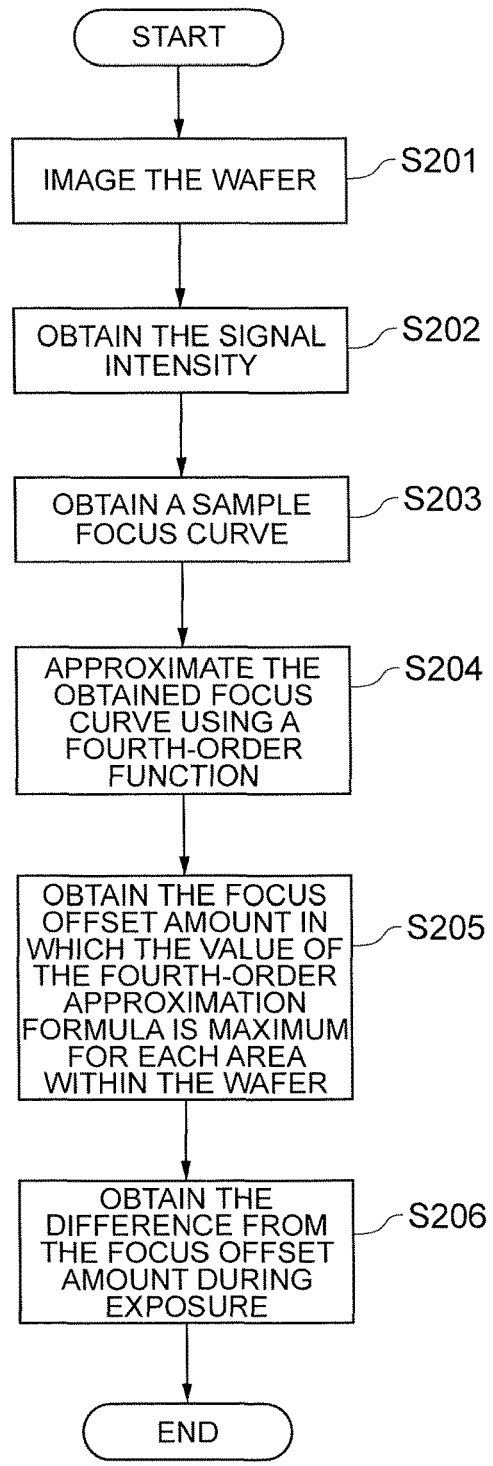
FIG. 17 a flowchart showing a method for determining the state of variation in the focus of the exposure device.

The image processing unit 40 is furthermore capable of determining the state of variation in the focus of the exposure device 100 for the entire surface of the wafer 10, i.e., focus monitor measurement, using a plurality of wafer images exposed and developed by varying the focus offset amount of the exposure device 100 for each wafer. In view of the above, a method for determining the state of variation in the focus of the exposure device 100 will be described with reference to the flowchart in FIG. 17. First, images of a plurality of wafers (here, for example, five wafers 15a to 15e in which the focus offset amount is −100 nm, −50 nm, 0 nm, +50 nm, and +100 nm) exposed and developed by varying the focus offset amount of the exposure device 100 for each wafer are acquired, as shown in FIG. 11A (step S201). At this point, the illumination, imaging, and the like of the wafer are carried out in the same manner as diffraction inspection. Herein, for convenience, the five wafers 15a to 15e having different focus offset amounts will be referred to as measurement wafers 15a to 15e.

Figure 11B:
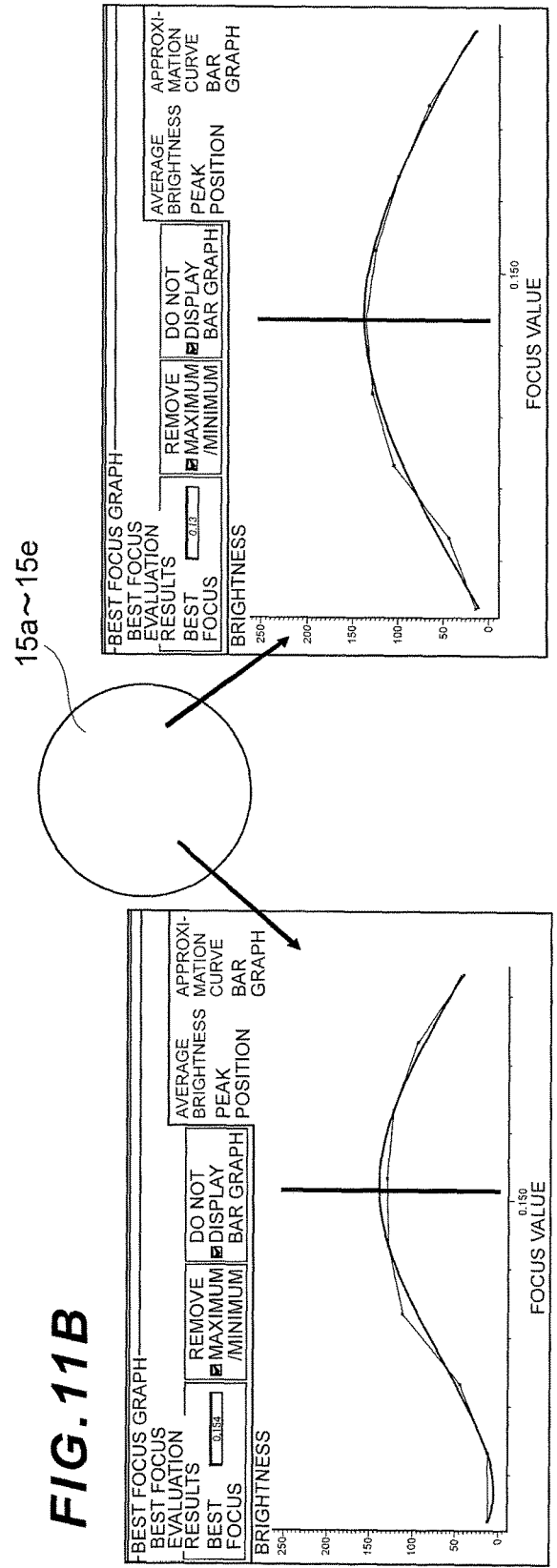

Next, the signal intensity for all of the shots within a wafer is determined in pixel units (or the average value of set areas formed by a small number of pixels, and the same applies hereinbelow) from the acquired wafer images for each of the measurement wafers 15a to 15e in which the focus offset amount of the exposure device 100 has been varied (step S202). Whether the signal intensity is obtained in pixel units or in set areas formed by a small number of pixels, the term set areas A shall be used for convenience, and the signal intensity (or average value) shall be referred to as average brightness. A plurality of set areas A was set for an exposure shot in the measurement of an image plane, but in the focus monitor measurement, a plurality of (plenty of) set areas A are set for the entire surface of the wafer, and the average value is determined for each of the set areas. Next determined is a graph showing the relationship between the average brightness in the set areas A in the same position on the wafers (that have mutually different focus offset amounts) and the focus offset amount corresponding thereto, i.e., a focus curve (referred to as a sample focus curve, as appropriate, hereinbelow in order to distinguish from the focus curve that serves as a reference determined using a condition-varied wafer), as shown in FIG. 11B (step S203). A fourth-order function is also preferably used as the approximation curve when a sample focus curve is to be approximated (step S204).

Figure 12:
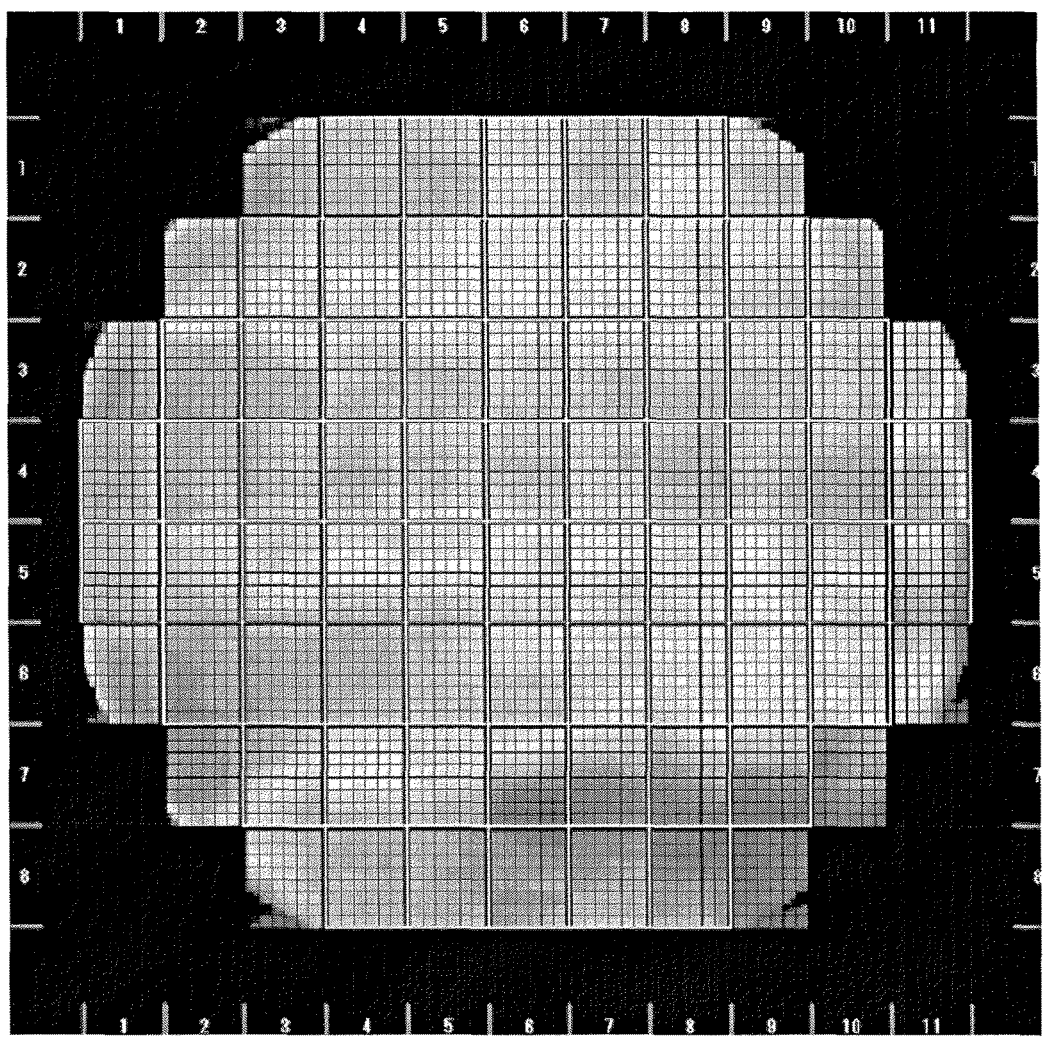
FIG. 12 is a view showing the distribution of shifts in the focus offset amount in the entire wafer.

Next, the image processing unit 40 determines for each set area the focus offset amount for which the average brightness is maximum on the approximate curve of the focus curve (step S205). In this manner, the distribution of the focus offset amount (the focus offset amount is converted to brightness in FIG. 12) for which the average brightness of the diffracted light is maximum on the wafer can be determined, as shown in FIG. 12. The difference between these values and the focus setting value during exposure is calculated for each of the set areas within the wafer (step S206), and the distribution of the focus state for the entire wafer, i.e., the measured value of the focus monitor is obtained. The method for measuring the image plane and the method for measuring the focus monitor described above, i.e., methods for determining the focus offset amount for which the approximate curve of the focus curve is maximum shall be referred to as peak methods for convenience.

In this manner, the distribution of the amount of displacement in the focus offset amounts on the wafer surface can be determined. Therefore, the state of variation in the focus of the exposure device 100 for the entire surface of the wafer 10 can be determined (e.g., see FIG. 12). In the present embodiment, an image of the entire wafer surface can be acquired in a lump, and the focus state of the entire surface of the wafer can therefore be measured in a very short period of time. In the example of FIG. 12, the state of variation in the focus of the exposure device 100 is expressed in light and dark areas, but the use of a pseudo-color display makes it possible to display large and small, and positive and negative displacements in focus in a single process by varying the colors. The state of variation in the focus (focus offset amount) of the exposure device 100 for the surface of the wafer 10 as determined using the image processing unit 40 can be sent from the image processing unit 40 to the exposure device 100 via a signal output unit (not shown) to provide feedback to the settings of the exposure device 100.

In this manner, in accordance with the present embodiment, the state of variation in the focus of the exposure device 100 can be determined on the basis of an image of a wafer exposed with a pattern used in production exposure, a pattern used in an actual device instead of a dedicated pattern can be employed, and since the illumination conditions of the exposure device 100 are not restricted, the focus state of the exposure device 100 can be measured with good precision. Naturally, a dedicated pattern may be used for adjustment or the like of the exposure device.

The focus state of the exposure device 100 can be measured with good precision because variations in the thickness of the resist film or the like are unlikely to have an impact when an image is captured using diffracted light generated from the surface of the wafer. It is particularly preferred that the wavelength of the illuminating light be 248 nm, 313 nm (j line), or other wavelengths in the deep UV region.

The focus state of the exposure device 100 can be determined using a plurality of diffraction conditions, and, e.g., averaging the diffraction conditions, whereby further improvement in precision can be expected. Also, selecting optimal diffraction conditions for each of various target patterns makes it possible to achieve highly sensitive and high-precision measurements. Abnormal values can be removed when averaging is carried out.

Also, when variation in diffraction brightness (i.e., the focus curve) is determined in relation to the focus offset amount, measurement sensitivity is improved when the exposure is carried out using a dose amount (exposure amount) that is slightly over or under the best dose amount. It is particularly effective to use an overdose amount. Such a method is also possible in the case that more precise measurement is required in periodic inspections or the like of the exposure device.

In the embodiment described above, the repeating pitch of patterns must be ½ or more of an illumination wavelength in order to occur diffraction. Accordingly, in the case that light having a wavelength of 248 nm is used as the illuminating light, diffracted light is no longer occurred with repeating patterns having a repeating pitch of 124 nm or less. However, even in such a case, if there are patterns having a repeating pitch greater than 124 nm (e.g., guard patterns or the like) in each position within a shot, measurement is possible because diffracted light is generated in those locations. The illumination conditions of exposure are set to conform to fine patterns. Therefore, the shape of patterns having a long repeating pattern as described above more readily degrades due to focus displacement (defocusing) in comparison with fine patterns, and, in other words, there are cases in which sensitivity to focus displacement is increased and measurement precision is enhanced.

In the embodiment described above, in terms of the pitch of the repeating patterns, the diffraction efficiency of higher-order diffracted light generally varies more greatly with respect to pattern variation in comparison with the use of first-order diffracted light. Therefore, sensitivity to variation in focus is improved, and the focus state (tendency of focus displacement or the state of variation in focus of the exposure device 100, as described above) during exposure can be measured with higher precision. In experiments carried out by the inventors of the present invention, effect is achieved using fourth-order diffracted light or greater, and there were also cases in which high precision could be obtained using $10^{th}$-order diffracted light and $120^{th}$-order diffracted light.

Figure 15:
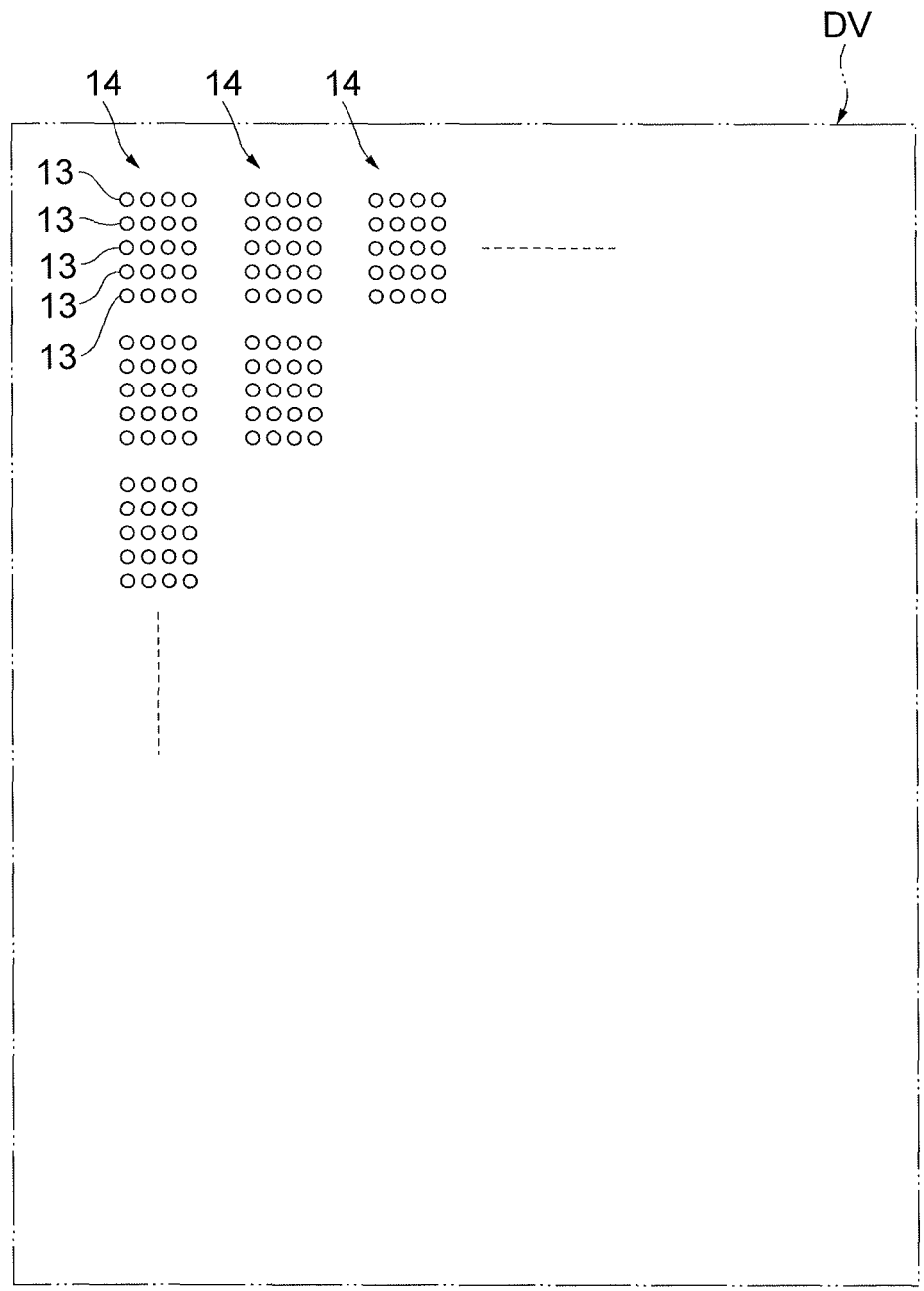
FIG. 15 is a schematic view of a pattern block composed of a plurality of holes.

There are also cases in which inspection can be carried out using diffracted light from repeating a pattern block, i.e., a group of patterns, even when the repeating pitch of the pattern is short and diffracted light does not emerge. For example, FIG. 15 shows the case of a semiconductor element DV (e.g., a memory element or the like) in which pattern blocks 14 composed of a plurality of holes 13 are longitudinally and laterally lined up. The inventors of the present invention found that when diffraction conditions are set so that $100^{th}$-order diffracted light is obtained from the pattern blocks 14 line up with a repeating pitch of 10 μm, the $100^{th}$-order diffracted light has high sensitivity with respect to variation in the shape (i.e., variation in the hole pattern) of the 60-nm diameter holes 13 lined up with a repeating pitch of 0.14 μm in the pattern blocks 14. Setting the diffraction conditions in this manner so that high-order diffracted light is obtained from a pattern having a relatively long repeating pitch makes it possible to detect pattern variations caused by defocusing of fine patterns (i.e., a pattern having a relatively short repeating pitch) in which diffracted light is unlikely to be generated, and the focus state during exposure can be measured with higher precision.

UV light having a short wavelength is preferably used as the illuminating light in order to obtain high-order diffracted light. In particular, the wavelength of the illuminating light is preferably 248 nm, 313 nm (j line), or other wavelengths in the deep UV region. Reducing the wavelength of the illuminating light in the case that the pitch of the repeating patterns is the same makes it possible to obtain high-order diffracted light using formula (1) described above. When there is a lower layer under the repeating pattern of the wafer, or when there is variability in the thickness of the lower layer film, the lower layer makes less impact when a shorter wavelength (e.g., 248 nm, 313 nm, or the like) is used for illuminating light.

In the case that high-order diffracted light is used, it is preferred that an image of a wafer (image by diffracted light) is captured over a plurality of times (e.g. 10 times) by the imaging device 35, then the image signals are sent to the image processing unit 40, and then a digital image of the wafer is generated or the focus state during exposure is determined on the basis of an integrated signal obtained by integrating a plurality of image signals from the imaging device 35. Since the reflectance is low in the case of high-order diffracted light, integrating the image signals increases the signal intensity, improves the SN ratio, and allows higher precision measurement of the focus state during exposure.

Dark current in the picture elements of the imaging device 35 can be measured in advance, and signals induced by the dark current can be removed when the image signals are integrated. The SN ratio can thereby be improved. For example, the integrated value Sa of the image signals from which dark current-induced signals have been removed is expressed as Sa=S−x {A×(N−1)}, where N is the number of imaging cycles, S is the integrated value of the image signals for N cycles, and A is the signal value of the dark current.

Furthermore, imaging time (exposure time) used by the imaging device 35 can be extended to increase the intensity of signals and improve the SN ratio. Also the imaging elements of the imaging device 35 may be cooled in order to reduce random noise in the picture elements.

In the embodiment described above, in addition to a wafer image (diffraction image) positioned by the stage 5 in a predetermined rotational position (first rotational position), it is possible to use the imaging device 35 to image the wafer image (diffraction image) positioned in a rotational position rotated 180 degrees (second rotational position) from the first rotational position, and to use the image processing unit 40 to correct the image rotation from the imaging device 35, average the image signals sent in each rotational position, generate a digital image of the wafer, and determine or otherwise assess the focus state during exposure. In such a configuration, measurement errors based on the asymmetry of the pattern shapes, or measurement errors based on the non-uniformity of illumination on the wafer can be reduced, and the focus state during exposure can therefore be measured with higher precision.

In the embodiment described above, it is also possible to capture the wafer image (diffraction image) over a plurality of times (e.g., 10 times) using the imaging device 35, and to use the image processing unit 40 to average the image signals sent over a plurality of times from the imaging device 35, generate a digital image of the wafer, and determine or otherwise assess the focus state during exposure. In such a configuration, the random noise of the picture elements is reduced by about $1/\sqrt{10}$ greater than a single imaging, and the focus state during exposure can therefore be measured with higher precision.

In the embodiment described above, the image plane of the exposure device 100 is measured on the basis of an image of the condition-varied wafer 10*a*, but no limitation is imposed thereby, and it is also possible to measure the image plane of the exposure device 100 using images of a plurality of exposed and developed wafers in which the focus offset amount of the exposure device 100 has been varied for each wafer (using the same conditions on the same wafer). In such a configuration, dynamic control errors (wafer stage scanning and leveling errors, reticle stage scanning and leveling errors, reticle stage and wafer stage synchronization errors, and other errors) produced each time the shot position is changed can be reduced, and the focus state during exposure can therefore be measured with higher precision.

In the embodiment described above, the exposure device 100 was a step-and-scan exposure device, but it is possible to obtain the same effect in the step-and-repeat exposure that dose not perform the stage scan nor reticle scan of the exposure device 100.

In the embodiment described above, errors are produced in the approximate curve with the presence of points where the curve is discontinuous or irregular variation is exhibited near the edge of the focus curve when an approximate curve (a quartic equation) of the focus curve is determined. Accordingly, when the parameters of the approximate curve are to be computed using the method of least squares, it is preferred that the impacts of discontinuous points or irregular points near the edge of the focus curve be reduced by weighting the measurement values, e.g., increasing the weighting of large points in the signal intensity on the focus curve and reducing the weighting of small points in the signal intensity.

In the embodiment described above, it is preferred that the illumination angle and the light-receiving angle in the selected illumination wavelength be selected so as to produce diffraction conditions in which the reflectance in relation to the resist film on which the patterns have been formed is near maximum or minimum. When the exposure amount (dose) is varied, the line width of the patterns varies and the actual thickness of the resist film on which the patterns have been formed varies. Accordingly, it is possible to reduce impacts caused by variation in the exposure amount because variations in reflectance in relation to variations in film thickness (variations in line width) are reduced by selecting diffraction conditions (illumination angle and light-receiving angle) in which the reflectance in relation to the resist film is near maximum or minimum by making use of the fact that the interference conditions (reflectance) of the reflected light vary in a periodic fashion in accordance with the thickness of the resist film.

Also, in the embodiment described above, the image plane and the focus state of the exposure device 100 are determined using diffracted light from the surface of the wafer, but no limitation is imposed thereby, and it is also possible to determine the image plane and the focus state of the exposure device 100 using regular reflectance from the surface of the wafer, variation in the state of polarized light, and the like.

Figure 4:
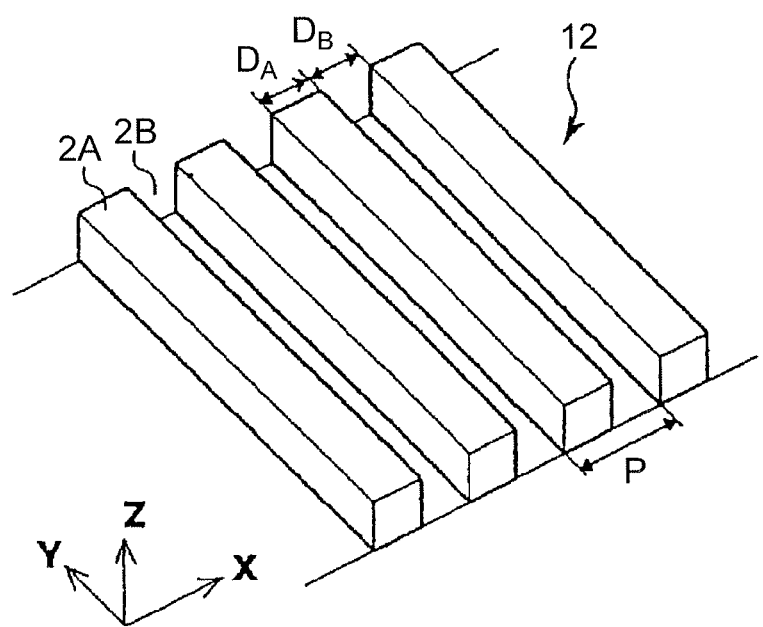
FIG. 4 is a perspective view illustrating the concave-convex structure of a repeating pattern.

The case in which PER inspection of the surface of the wafer 10 is carried out using the surface inspection apparatus 1 will now be described. The repeating pattern 12 is a resist pattern (line pattern) in which a plurality of line parts 2A are arrayed at a constant pitch P along the crosswise direction (X direction) of the repeating pattern, as shown in FIG. 4. The areas between mutually adjacent line parts 2A are space parts 2B. The arrayed direction (X direction) of the line parts 2A shall be referred to as "the repeating direction of the repeating pattern 12."

In this case, the design value of the width $D_A$ of the line parts 2A in the repeating pattern 12 is ½ of the pitch P. In the case that the repeating pattern 12 has been formed in accordance with design values, the width $D_A$ of the line parts 2A and the width $D_B$ of the space parts 2B will be equal and the volume ratio of the line parts 2A and the space parts 2B will be substantially 1:1. In contrast, when the exposure focus is outside the optimum values when the repeating pattern 12 is formed, the pitch P does not change, but the width $D_A$ of the line parts 2A differs from the design values, the width $D_B$ of the space parts 2B are also different, and the volume ratio of the line parts 2A and the space parts 2B deviates from substantially 1:1 ratio.

A PER inspection inspects for abnormalities in the repeating pattern 12 using variations in the volume ratio between the line parts 2A and the space parts 2B in a repeating pattern 12 such as that described above. In order to simplify description, the ideal volume ratio (design values) shall be 1:1. Variations in the volume ratio are due to values that are deviated from the optimum values of exposure focus and such variation appear in each shot area of the wafer 10. The volume ratio can also be stated as the area ratio of the cross-sectional shape.

Figure 5:
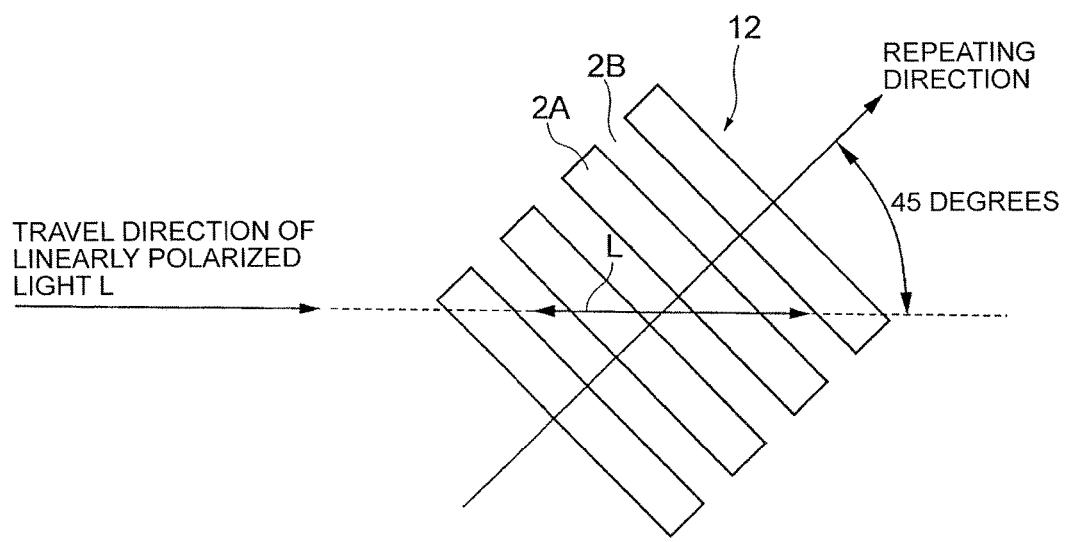
FIG. 5 is a view illustrating the tilt state between the incident plane of linearly polarized light and the repeating direction of the repeating pattern.

In a PER inspection, the illumination-side polarizing filter 26 and the light-receiving-side polarizing filter 32 are inserted in the optical path, as shown in FIG. 2. When PER inspection is carried out, the stage 5 tilts the wafer 10 at a slope angle that allows regular reflectance from the wafer 10 irradiated with illuminating light to be received by the light-receiving system 30, stops the wafer at a predetermined rotational position, and holds the wafer so that the repeating direction of the repeating pattern 12 on the wafer 10 is tilted 45 degrees with respect to the direction of vibration of the illuminating light (linearly polarized light L) on the surface of the wafer 10, as shown in FIG. 5. This is done to maximize the signal intensity of the inspection of the repeating pattern 12. Also, the sensitivity of the inspection is increased when the angle is 22.5 degrees or 67.5 degrees. The angle is not limited to these angles, and it is also possible to set an arbitrary angular direction.

The illumination-side polarizing filter 26 is arranged between the light-guide fiber 24 and the illumination-side concave mirror 25, has the transmission axis thereof in a predetermined orientation (direction), and extracts (transmits) a polarized light component (linearly polarized light) from the light from the illumination unit 21 in accordance with the transmission axis. At this point, since the exit part of the light-guide fiber 24 is arranged in the focal position of the illumination-side concave mirror 25, the illumination-side concave mirror 25 forms the light transmitted through the illumination-side polarizing filter 26 into parallel luminous flux and illuminates the wafer 10, which is a semiconductor substrate. In this manner, the light emitted from the light-guide fiber 24 passes through the illumination-side polarizing filter 26 and the illumination-side concave mirror 25 to become linearly p-polarized light L (see FIG. 5), and is irradiated onto the entire surface of the wafer 10 as illuminating light.

The direction of travel of the linearly polarized light L (the direction of the principal rays of the linearly polarized light L that arrives at an arbitrary point on the surface of the wafer 10) is substantially parallel to the optical path, and the incident angles of the linearly polarized light L at each point on the wafer 10 are therefore mutually the same because of the parallel luminous flux. Also, the linearly polarized light L incident on the wafer 10 is p-polarized light, and the angle formed by direction of vibration of the linearly polarized light L at the surface of the wafer 10 and the repeating direction of the repeating pattern 12 is therefore also set to 45 degrees, as shown in FIG. 5, in the case that repeating direction of the repeating pattern 12 has been set to an angle of 45 degrees with respect to the plane of incidence of the linearly polarized light L (the travel direction of the linearly polarized light L at the surface of the wafer 10). In other words, the linearly polarized light L is incident on the repeating pattern 12 so as to obliquely transverse the repeating pattern 12 in a state in which the direction of vibration of the linearly polarized light L at the surface of the wafer 10 is tilted 45 degrees with respect to the repeating direction of the repeating pattern 12.

The regular reflectance reflected by the surface of the wafer 10 is collected by the light-receiving-side concave mirror 31 of the light-receiving system 30 and arrives at the imaging plane of the imaging device 35, and at this point, the polarized state of the linearly polarized light L is changed (changed into elliptically polarized light) by the structural birefringence of the repeating pattern 12. The light-receiving-side polarizing filter 32 is arranged between the light-receiving-side concave mirror 31 and the imaging device 35, the azimuth of the transmission axis of the light-receiving-side polarizing filter 32 is set so as to be orthogonal to the transmission axis of the illumination-side polarizing filter 26 described above (a crossed Nicols state). Therefore, a linearly polarized light component (e.g., s-polarized component) having a direction of vibration that is substantially orthogonal to the linearly polarized light L in the regular reflectance from the wafer (the repeating pattern 12) can be extracted by the light-receiving-side polarizing filter 32 and directed to the imaging device 35. As a result, a reflected image of the wafer 10 is formed on the imaging plane of the imaging device 35 by the polarized light component having a direction of vibration that is substantially orthogonal to the linearly polarized light L in the regular reflectance from the wafer 10. In the case that the minor axis direction of the elliptically polarized light is not orthogonal to the linearly polarized light L, sensitivity can be improved by bringing the transmission axis of the light-receiving-side polarizing filter 32 into conformity with the minor axis direction of the elliptically polarized light.

In order to perform a PER inspection of the surface of the wafer 10 using the surface inspection apparatus 1, first, the illumination-side polarizing filter 26 and the light-receiving-side polarizing filter 32 are inserted into the optical path, as shown in FIG. 2, and the wafer 10 is transported onto the stage 5 by a transport device (not shown). The position information of the patterns formed on the surface of the wafer 10 is acquired by an alignment mechanism (not shown) at an intermediate point during transport, and the wafer 10 can be mounted in a predetermined direction in a predetermined position on the stage 5. Also, at this point, the stage 5 tilts the wafer 10 at a slope angle that allows regular reflectance from the wafer 10 irradiated with illuminating light to be received by the light-receiving system 30, stops the wafer at a predetermined rotational position, and holds the wafer so that the repeating direction of the repeating pattern 12 on the wafer 10 is tilted 45 degrees with respect to the direction of vibration of the illuminating light (linearly polarized light L) on the surface of the wafer 10.

Next, the illuminating light is irradiated onto the surface of the wafer 10. When the illuminating light is to be irradiated onto the surface of the wafer 10 in such conditions, the light emitted from the light-guide fiber 24 of the illumination unit 21 passes through the illumination-side polarizing filter 26 and the illumination-side concave mirror 25 to become linearly p-polarized light L, and is irradiated onto the entire surface of the wafer 10 as illuminating light. The regular reflectance reflected by the surface of the wafer 10 is collected by the light-receiving-side concave mirror 31 and arrives at the imaging plane of the imaging device 35, and an image of the wafer 10 (reflection image) is formed.

At this point, the polarized state of the linearly polarized light L is changed by the structural birefringence of the repeating pattern 12. The light-receiving-side polarizing filter 32 can extract and direct a polarized light component having a direction of vibration that is substantially orthogonal (i.e., a change in the state of polarization of the linearly polarized light L) to the linearly polarized light L in the regular reflectance from the wafer 10 (the repeating pattern 12) to the imaging device 35. As a result, a reflected image of the wafer 10 is formed on the imaging plane of the imaging device 35 by the polarized light component having a direction of vibration that is substantially orthogonal to the linearly polarized light L in the regular reflectance from the wafer 10.

As a result of the above, the imaging device 35 photoelectrically converts the image (reflection image) of the surface of the wafer 10 formed on the imaging plane to generate an image signal and outputs the image signal to the image processing unit 40. The image processing unit 40 generates a digital image of the wafer 10 on the basis of the image signal of the wafer 10 received from the imaging device 35. When an image (digital image) of the wafer 10 has been generated, the image processing unit 40 compares the image data of the wafer 10 and the image data of a non-defective wafer, and inspects for the existence of defects (abnormalities) in the surface of the wafer 10. The signal intensity (brightness value) of the reflected image of the non-defective wafer, i.e., a wafer exposed and developed in a state of best focus and best dose, is thought to show the highest signal intensity (brightness value), and therefore, e.g., variation in the signal intensity (variation in the brightness) that is greater than a threshold value (permissible value) set in advance in comparison with a non-defective wafer is assessed to be "abnormal," and a signal intensity that is less than the threshold value is determined to be "normal." The detection results obtained by the image processing unit 40 and the corresponding image of the wafer 10 are sent and displayed on an image display device (not shown).

The image processing unit 40 can determine a focus curve of the exposure device 100 from the polarized light using the image of the wafer exposed and developed in conditions in which the focus offset amount of the exposure device 100 has been varied for each shot. The tilt of the image plane of the patterns projected and exposed by the exposure device 100 can be determined in the same manner as when diffracted light is used by determining the focus offset amount in which the signal intensity (the above-described average brightness) of the detected polarized light is maximum using the focus curve. Specifically, in step S103 of the flowchart shown in FIG. 6, the linearly polarized light L is irradiated onto the surface of the condition-varied wafer 10a as illuminating light, the imaging device 35 photoelectrically converts the reflection image of the condition-varied wafer 10a to generate an image signal, and the image signal is sent to the image processing unit 40. In the case of polarized light, the focus offset amount in which the signal intensity is maximum is thought to be the best focus, and it is therefore possible to readily know the focus offset amount of the best focus.

By performing illumination, image capture and other process in relation to the wafer in the same manner as PER inspection, the image processing unit 40 can furthermore determine the focus curve of the average brightness (with constant illumination conditions) of the polarized light using images of a plurality of wafers exposed and developed by varying the focus offset amount of the exposure device 100 for each wafer. The state of the focus curve of the exposure device 100 on the surface of the wafer 10 can thereby be determined, i.e., focus monitor measurement can be carried out.

The azimuth of the transmission axis of the light-receiving-side polarizing filter 32 can be slightly displaced from the orthogonal state with respect to the transmission axis of the above-described illumination-side polarizing filter 26 and made to adjust by amount of structural birefringence-induced rotation of the polarized illuminating light.

Figure 16:
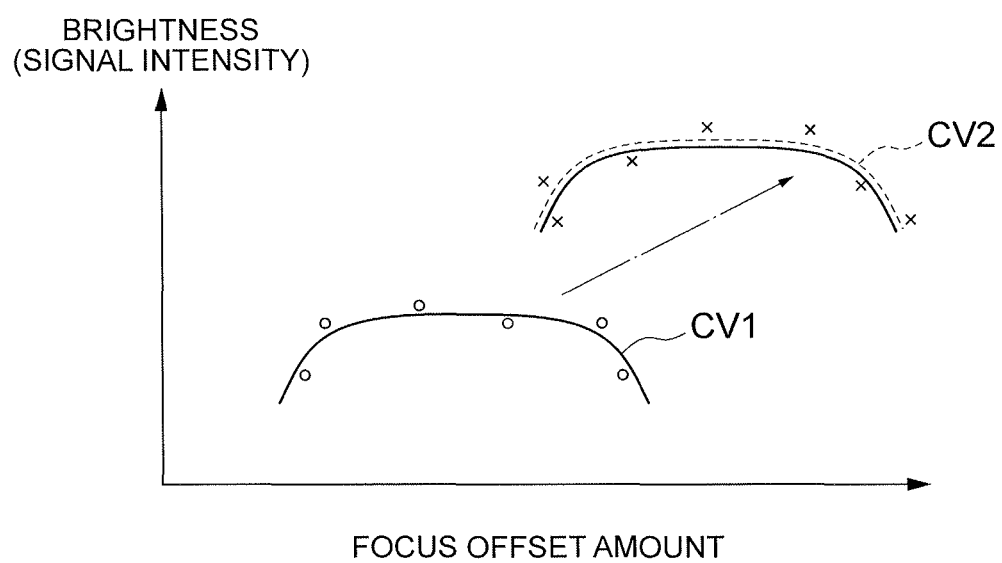
FIG. 16 is a view showing an example of fitting while varying gain.

In the embodiment described above, focus monitor measurement is carried out by the peak method, but it is also possible to carry out focus monitor measurement using another method. Depending on the pattern, there are cases in which the vicinity of the maximum value of the focus curve has a flat shape. For example, there are cases in which the shape is that of the focus curves CV1, CV2 shown in FIG. 16. In this case, it is difficult to determine with good precision the focus offset amount at which the signal intensity is maximum, and the measurement precision is reduced as a result with the peak method of the first embodiment.

An effective method for such a case will now be described in a second embodiment of the present invention. In the second embodiment, the device configuration, the method for exposing the wafer, and other features are essentially the same as the first embodiment. Therefore, a detailed description of the surface inspection apparatus of the second embodiment will be omitted. The difference between the first embodiment and the second embodiment is that the method for measuring the focus state was the peak method in the first embodiment, but a method referred to for convenience as the fitting method will be used in the second embodiment.

Figure 18:
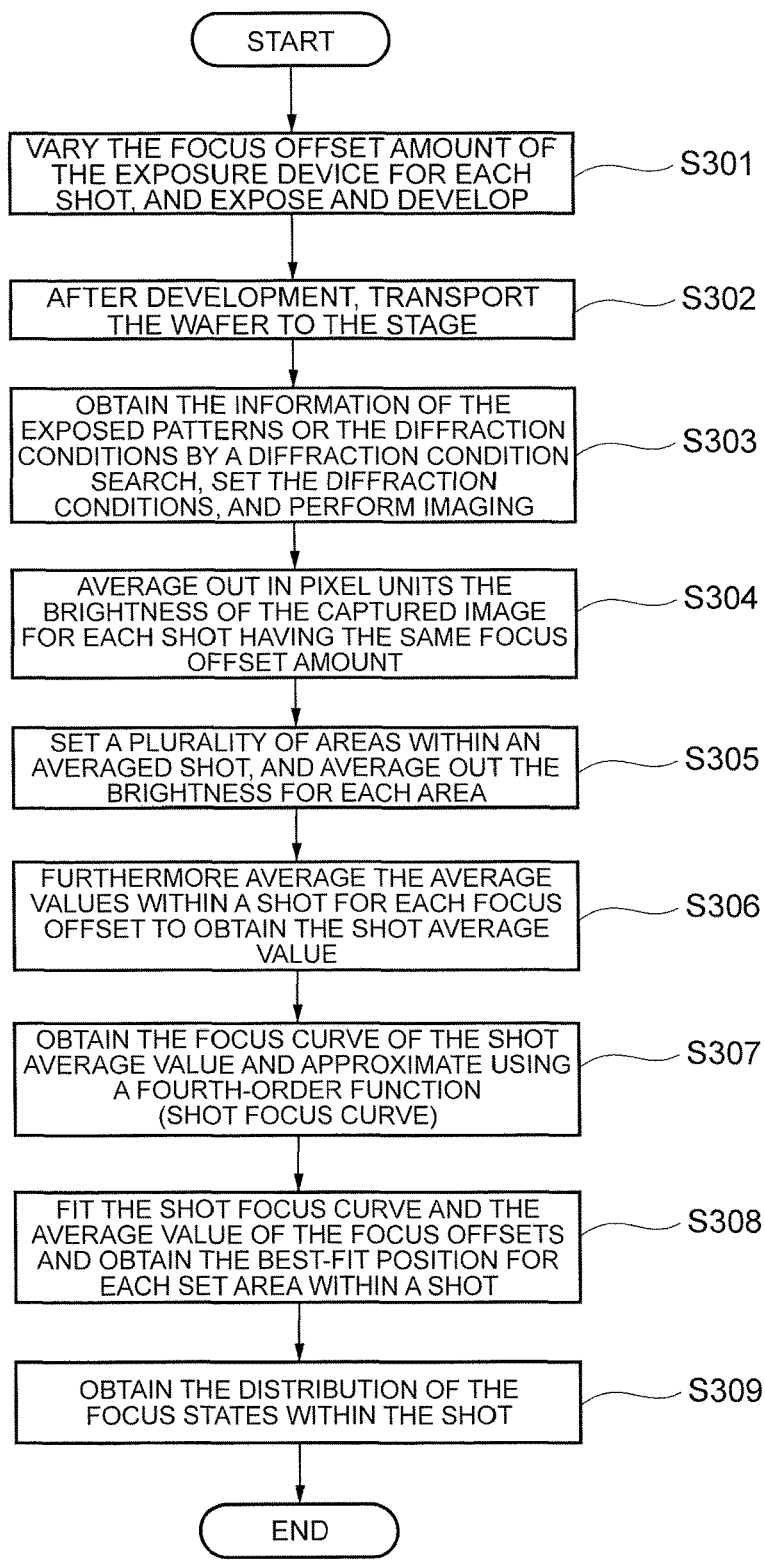
FIG. 18 is a flowchart showing a method for determining by fitting the tilt of the image plane.

First, the procedure for measuring the image plane using the fitting method will be described with reference to the flowchart shown in FIG. 18. Steps S301 to S305 of FIG. 18 are the same process as steps S101 to S105 of FIG. 6. A description of portions having the same process are omitted. However, in relation to each shot in which a focus offset has been varied, the average brightness is determined for each of a plurality of set areas within the shot through step S305. Next, in further relation to each shot in which a focus offset has been varied, the average values (average brightness) of all the set areas within a shot are averaged to determine the shot average value (step S306). Next, a focus curve that expresses the relationship between the shot average value and the focus offset is determined (hereinafter referred to as the shot focus curve in order to distinguish from other focus curves), and the shot focus curve thus determined is approximated using an approximate curve of a fourth-order function (step S307). One shot focus curve is obtained from one condition-varied wafer.

Figure 20:
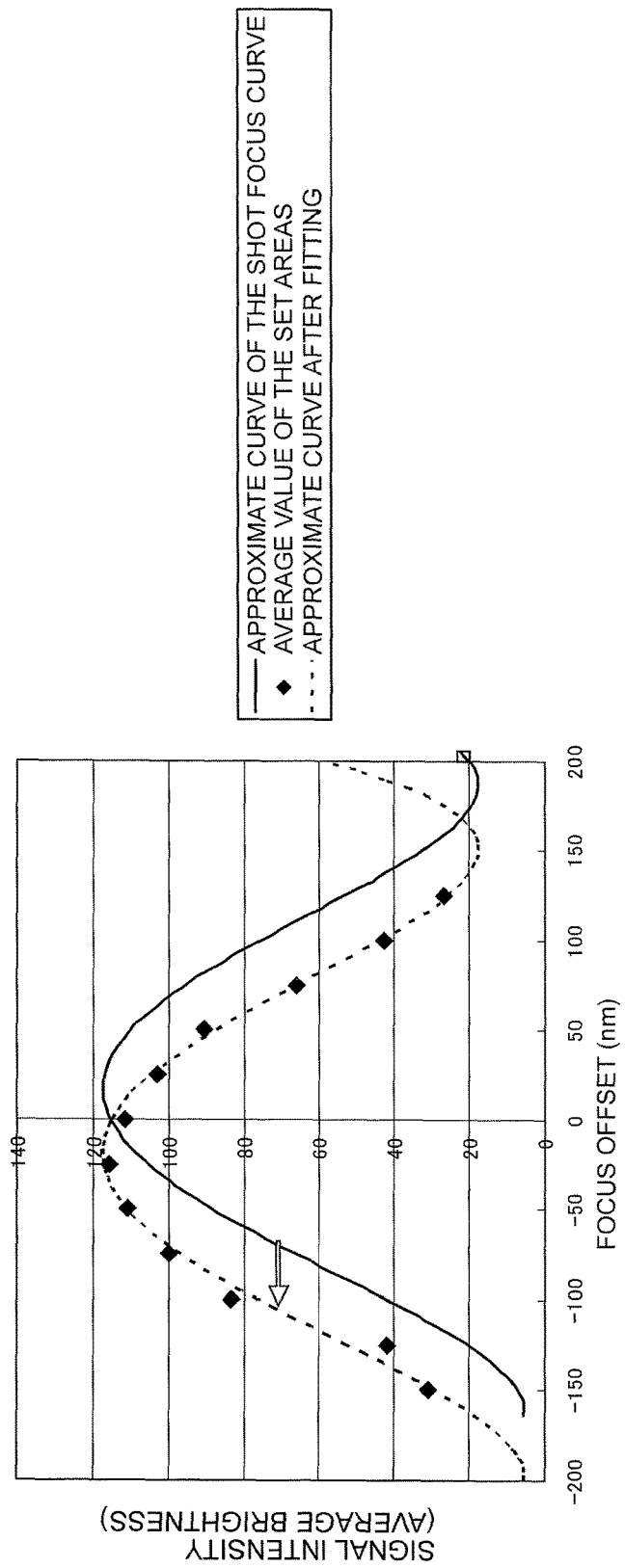
FIG. 20 is a view showing an example of fitting.

Next, the average value (average brightness) in relation to the focus offsets determined in step S305 and the shot focus curve determined in step S307 are fitted for each of the set areas within a shot, and the position (on the graph) of the best-fit shot focus curve is determined (step S308). As used herein, the term 'fitting' refers to calculating the degree of conformity with the average brightness expressed by the diamond markers in the graph shown in FIG. 20 while the approximate curve of the shot focus curve shown by the solid line is moved to right or left i.e., changing the focus offset in increments of, e.g., 1 nm to determine the best-fit position, and the movement distance from the original shot focus curve (the difference of the focus offset) is the measured value of the set areas (expressing the focus state). It is possible to calculate the sum of squares of the difference between the average brightness and the value of the approximate curve at the same focus offset as the degree of conformity and to determine the position at which the sum of squares is minimum, and it is possible to determine the correlation coefficient and determine the position at which the correlation coefficient is maximum.

By a peak method, the focus curve is determined for each of the set areas and the focus state is determined from the focus offset of the maximum value of the focus curves. However, by the fitting method, the difference in the position of the average brightness is determined for each of the set areas in relation to one reference shot focus curve to determine the focus state. Determining the distribution of the focus state within a shot (step S309) allows the measurement of image plane using the fitting method.

Figure 19:
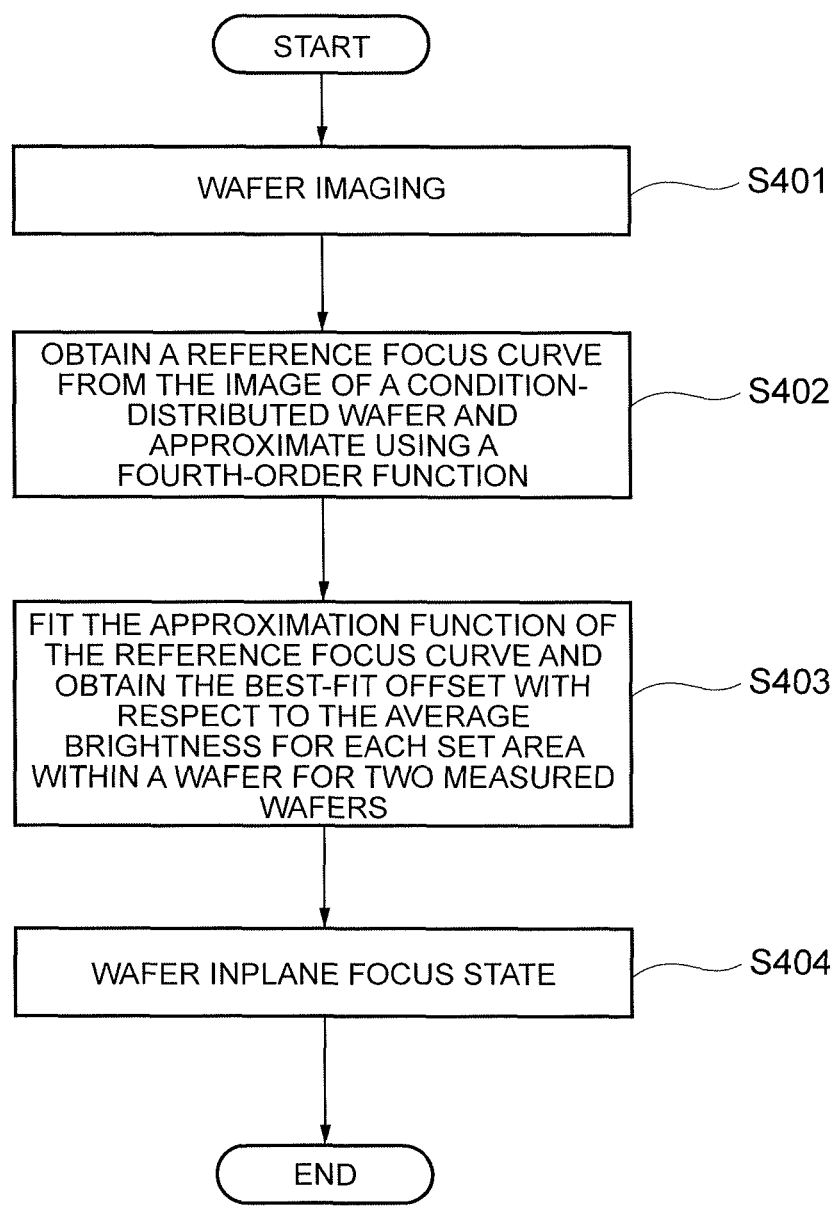
FIG. 19 is a flowchart showing a method for determining by fitting the state of variation in the focus.

The procedure for performing focus monitor measurement using the fitting method will be described with reference to the flowchart shown in FIG. 19. One condition-varied wafer fabricated in the same manner as that used for image plane measurement, and two wafers (for convenience, hereinafter referred to as measurement wafer) exposed and developed using two predetermined types of focus offset amounts (e.g., −100 nm and −50 nm) for a total of three wafers will be used in focus monitor measurement using the fitting method.

Figure 21:
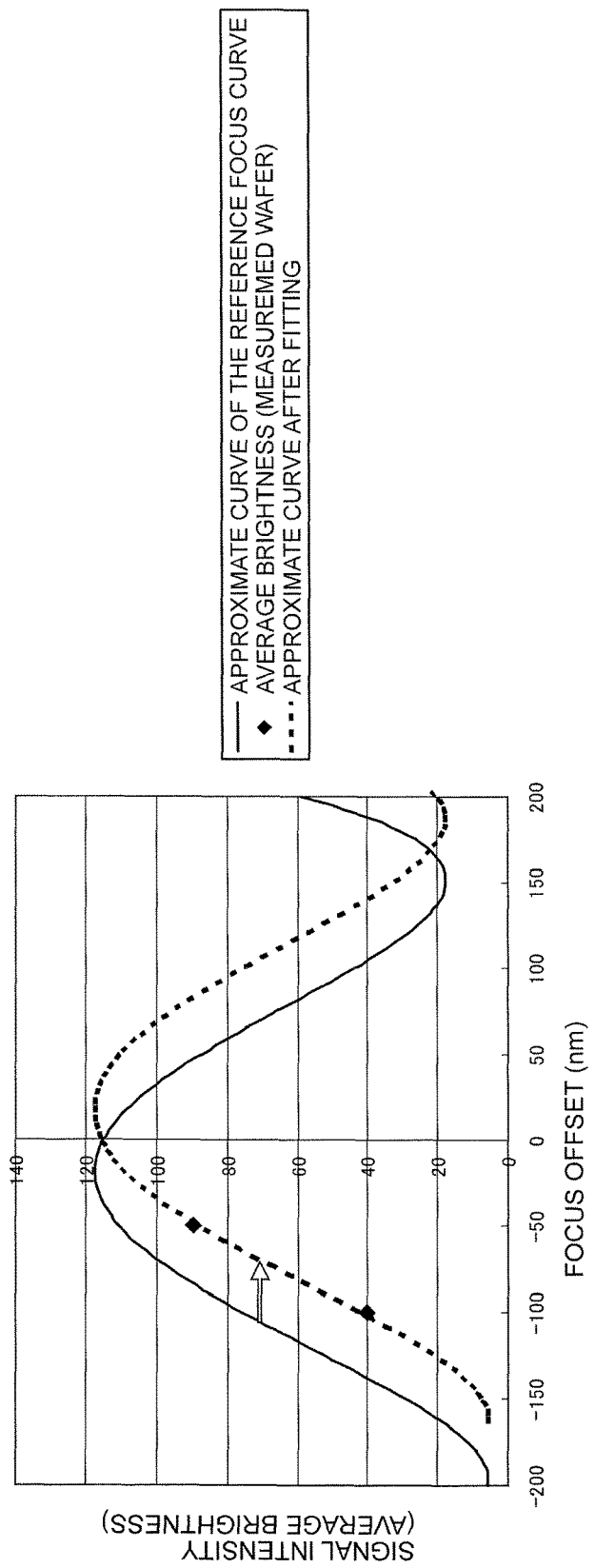
FIG. 21 is a view showing an example of fitting.

First, images of the one condition-varied wafer and the two measurement wafers are acquired (step S401). Next, a reference focus curve (the same as that described in the first embodiment) is determined from the image of the condition-varied wafer for each of the plurality of set areas set within an exposure shot using the same method as used for image plane measurement, and the reference focus curve thus determined is approximated using an approximate curve of, e.g., a fourth-order function (step S402). Next, the average brightness is determined for each of the plurality of set areas within the wafer plane of the measurement wafer and fitted to the approximate curve of the reference focus curve (step S403), and the results are sent (step S404). FIG. 21 is a view for describing an example of fitting in a certain set area. In FIG. 21, the curve shown by a solid line in the graph is an approximate curve of the reference focus curve, and the diamond markers are the average brightness of the measurement wafers. The curve shown by the broken line is the result of displacing the approximate curve in the lateral direction of the graph to determine the position that best fits the average brightness, and the movement distance in the lateral direction, i.e., the difference in focus offset is the measurement value that expresses the focus state of this set area.

Specifically, with fitting in focus monitor measurement, the difference between approximate curve and the signal intensity (average brightness) of the measurement wafers is determined while the approximate curve is displaced (laterally) in increments of, e.g., 1 nm in terms of the focus offset amount for each of the set areas, and the sum of squares of the differences for the measurement wafers can be calculated to determine the position in which the sum of squares is minimum. It is also possible to calculate the correlation coefficient while displacing the approximate curve to determine a position in which the correlation coefficient is maximum.

It is preferred that the set areas within a shot for determining the reference focus curve and the set areas within the measurement wafers have the same position in a shot, and the reference focus curve by each of the set areas in which the position within the shot is the same as the set areas of the measurement wafers is preferably used when the above-described fitting is carried out. A reference focus curve is not used by way of limitation, it also being possible to use a shot focus curve determined by measuring the image plane. The focus state of the entire wafer, excluding the variation component of the image plane of the shot, can be measured when a reference focus curve is used for each of the set areas. In contrast, the focus state of the entire surface of the wafer, including the variation component of the image plane, can be measured when a shot focus curve is used. In other words, these focus curves can be selectively used in accordance with the application.

Using such a configuration makes it possible to perform focus monitor measurement using one condition-varied wafer and two measurement wafers. By the fitting method, measurement can be carried out with high precision because fitting is carried out for the entire curve, even when the vicinity of the maximum value of the focus curve is flat. The fitting method is also advantageous in that measurement can be carried out with few wafers required for measurement.

Figure 22:
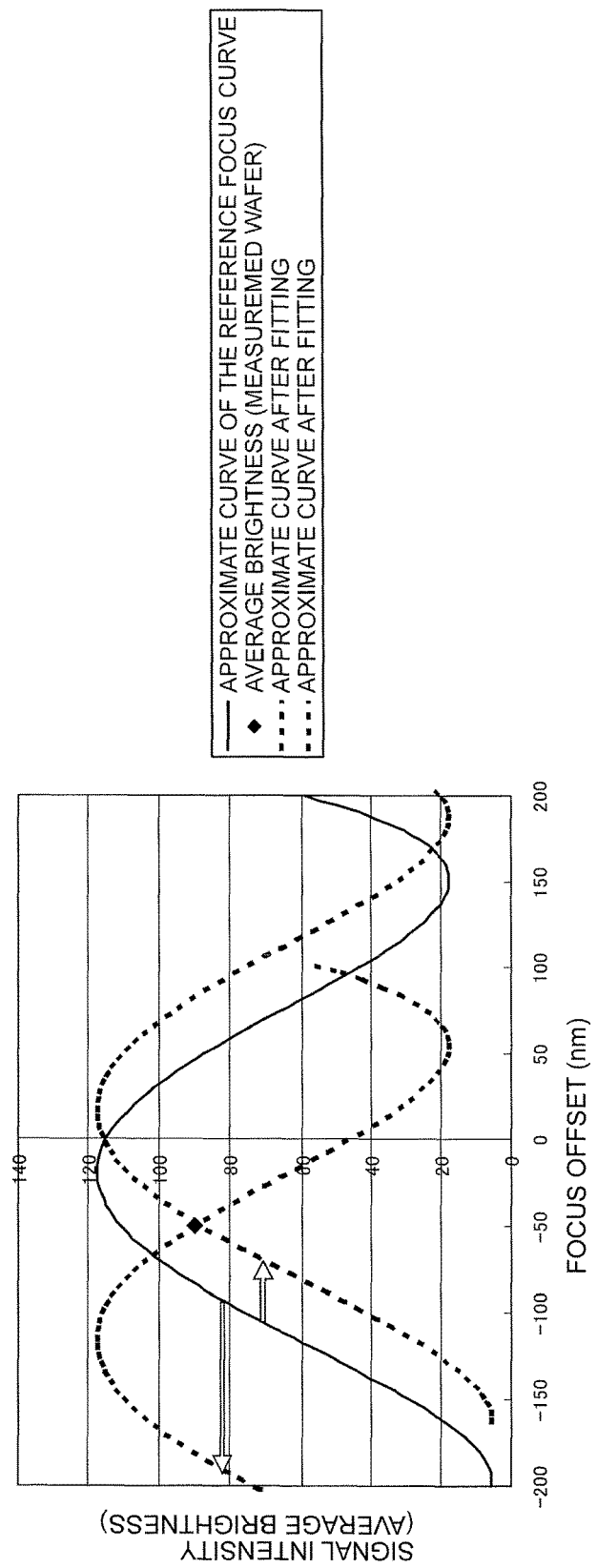
FIG. 22 is a view showing an example of fitting when the number of wafers is a single wafer.

In the embodiment described above, two measurement wafers were used, but the number of measurement wafers is not limited to two thereby, and it is also possible to use more than two measurement wafers. Measurement can be performed with greater stability using a larger number of measurement wafers. Measurement cannot be performed with a single measurement wafer because two matching positions are available for fitting, as shown in FIG. 22.

There are cases in which the brightness of the image slightly varies due to a slight difference in the thickness of the resist film or the dose amount between the condition-varied wafer and the measurement wafers. However, in such a case, a gain is applied to the signal intensity of the approximate curve, and results with higher precision can be determined when fitting is carried out in conformity with the brightness. The value of the gain may be a fixed value obtained from an image of the wafer. It is also possible to carry out fitting while the gain is varied, and to simultaneously obtain: the gain having the smallest divergence of average brightness from the approximate curve; and the movement distance (i.e., the difference in focus offset) in the lateral direction of the approximate curve (e.g., see FIG. 16).

In the above-described second embodiment as well, it is possible to carry out measurement using not only diffracted light, but also variation in the state of polarization in the same manner as the first embodiment, and it is also effective to integrate and average images, use high-order diffracted light and a short wavelength, and apply other means for improving precision described in the first embodiment.

In the first and second embodiments described above, the focus state during exposure is determined, but no limitation is imposed thereby, and it is also possible to determine the dose state during exposure. A third embodiment of the present invention will now be described. In the third embodiment, variation in the dose (exposure amount) is determined using a diffraction inspection technique. A dose is the amount of energy used when a pattern is formed. In the third embodiment, the device configuration, the method for exposing the wafer, and other features are essentially the same as the first embodiment. Therefore, a detailed description of the surface inspection apparatus of the third embodiment will be omitted.

Figure 23:
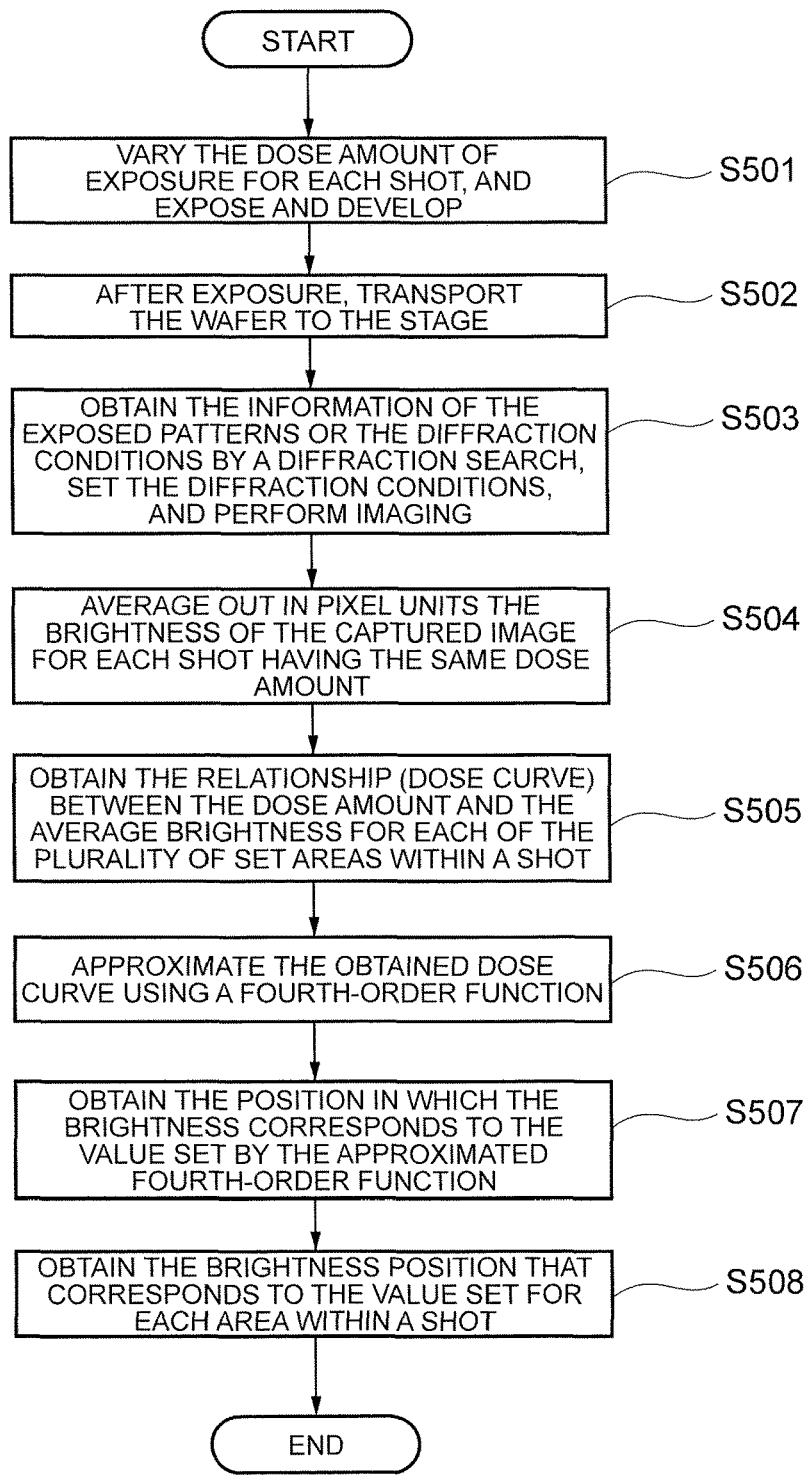
FIG. 23 is a flowchart showing a method for determining the state of variation of the dose in the exposure device.

The method for determining the state of variation in the dose of the exposure device 100 will be described with reference to the flowchart in FIG. 23. First, a wafer on which a repeating pattern has been formed by varying the dose amount of the exposure device 100 is fabricated (step S501). At this point, the dose amount is varied in a random fashion for each exposure shot to carry out exposure and development. Hereinbelow, such a wafer shall be referred to as a dose condition-varied wafer. The dose amount is varied in a random manner with the aim of offsetting differences in the resist conditions generated between the center side and the external peripheral side of the wafer, crosswise differences during scan exposure, and other impacts.

The dose condition-varied wafer of the present embodiment has dose amounts varied in eight steps of 1.5 mJ increments (10.0 mJ, 11.5 mJ, 13.0 mJ, 14.5 mJ, 16.0 mJ, 17.5 mJ, 19.0 mJ, and 20.5 mJ). The exposure amount required for pattern exposure is about 5 mJ to 40 mJ depending on the pattern, and the step used when fabricating a dose condition-varied wafer is preferably 0.5 mJ to 2.0 mJ.

A plurality of dose condition-varied wafers may be fabricated to obtain a dose curve. In such a case, the arrangement of shots for each dose amount of the condition-varied wafers is preferably set so as to cancel impacts induced by conditions other than the dose amounts.

When a dose condition-varied wafer is fabricated, the dose condition-varied wafer is transported on the stage 5 in the same manner as diffraction inspection (step S502). Next, illuminating light is irradiated onto the surface of the dose condition-varied wafer in the same manner as diffraction inspection. The imaging device 35 photoelectrically converts the diffraction image of the dose condition-varied wafer to generate an image signal, and outputs an image signal to the image processing unit 40 (step S503). At this point, the diffraction conditions are determined for the dose condition-varied wafer using the pitch information of the exposed pattern or a diffraction condition search, and settings are made in the same manner as diffraction inspection so that diffracted light can be obtained. A diffraction condition search refers to a function for varying the tilt angle of the stage 5 a stepwise fashion in an angle range that excludes normal reflectance to acquire an image at each of the tilt angles, and determining the tilt angle at which the image brightens, i.e., the tilt angle at which diffracted light is obtained. The azimuth angle (the orientation with respect to illumination direction of the illuminating light of the exposed pattern) of the dose condition-varied wafer is arranged so that the illumination direction matches the repeating direction of the exposed pattern (the direction orthogonal to the line in the case of a line-and-space pattern).

Next, the image processing unit 40 generates a digital image of the dose condition-varied wafer on the basis of the image signal of the dose condition-varied wafer received from the imaging device 35, and averages out the signal intensity (brightness) in pixel units (the pixels of the corresponding portions of each shot) for each shot for which the dose amount is the same (step S504). The portions determined to be defective in the diffraction inspection are excluded from the above-described averaging. The image processing unit 40 then determines the average value (for convenience, hereinafter referred to as average brightness) of the signal intensity in a plurality of set areas (areas enclosed by small rectangles) A set within a shot for all of the shots obtained by averaging (mutually different in dose amounts), as shown in FIG. 8. The dose condition-varied wafer is configured so that the dose amount can be determined from the position of the shot because the dose amount of the exposure device 100 is varied for each shot, and the average brightness varies in accordance with the dose amount in set areas of the same position within each shot exposed using a different dose amount.

Figure 24:
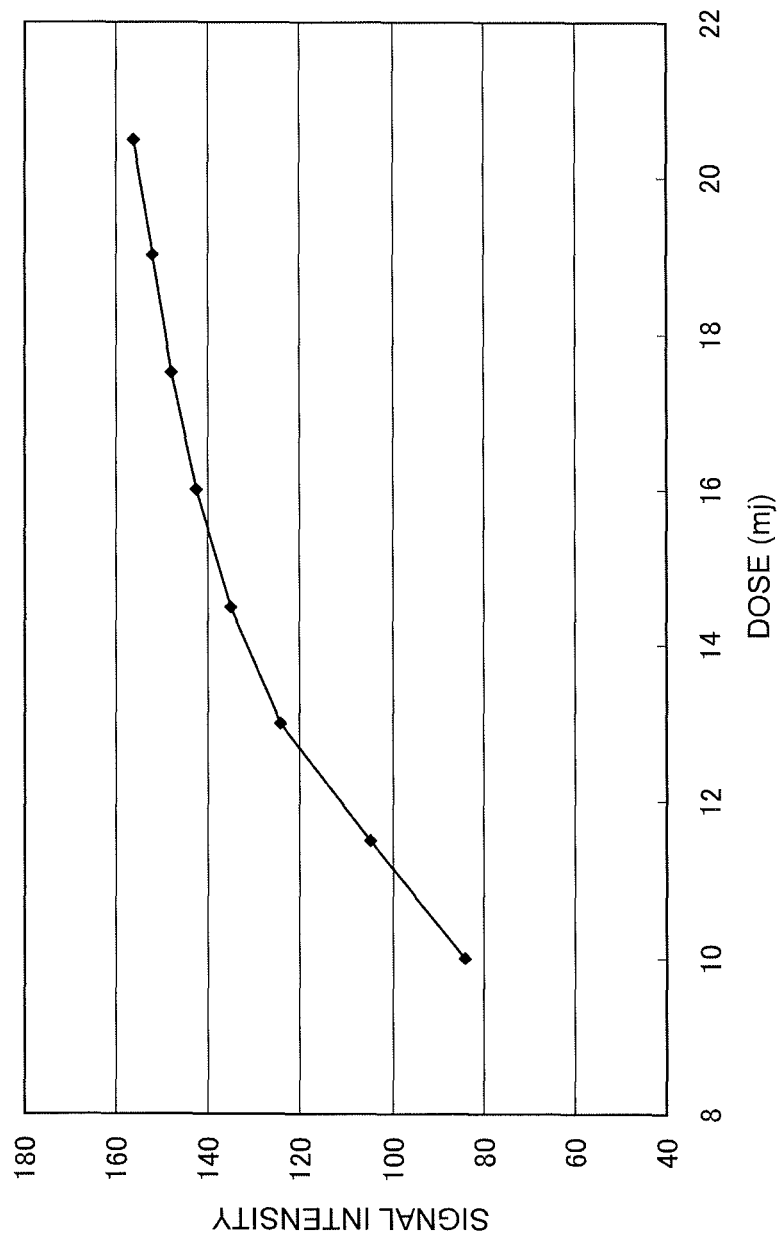
FIG. 24 is a view showing an example of a dose curve.

In view of the above, the image processing unit 40 determines the average brightness in the set areas in the same position in each shot (which mutually differ in dose amount) for each of the set areas for which the average brightness was determined, and a graph, i.e., a dose curve showing the relationship with corresponding dose amount is determined (step S505). An example of a dose curve is shown in FIG. 24.

Next, the image processing unit 40 determines an approximate curve in which the dose curve has been approximated using a function for each of the set areas (step S506). A forth-order function (a quartic equation) is preferably used as the function of the approximate curve. Also, the dose curve thus determined in this case shall be referred to as a reference dose curve. The fourth-order function is the same as that of a focus curve, and a description is omitted.

Next, the image processing unit 40 determines the dose amount which will produce the brightness that corresponds to the design value on the approximate curve of the dose curve (step S507). At this point, the dose amount which will produce the brightness that corresponds to the design value is determined for each of the set areas (step S508). The distribution of the dose amount within a shot can be determined in this manner. The brightness (signal intensity) that corresponds to the design value on the approximate curve of the dose curve is determined in advance using a pattern in which the line width conforms to the design value.

The state of variation of the dose in the image plane of the pattern projected and exposed by the exposure device 100 is determined on the basis of the distribution of the dose amounts in which the brightness of the diffracted light will be a brightness that corresponds to the design value within a shot. The state of variation of the dose in the image plane determined in this manner is converted to, e.g., a parameter compatible with the exposure device 100, is sent from the image processing unit 40 to the exposure device 100 via the signal output unit 90, or is used to adjust the optical system and be reflected in the exposure carried out by the exposure device 100.

Using such a configuration makes it possible to measure the state of variation in the dose amount of the exposure device 100 with good precision in a short period of time on the basis of an image of a wafer exposed using a pattern used in production exposure, by capturing the image of the wafer on which a repeating pattern is fabricated and the dose of the exposure device 100 is varied.

The state of variation in the dose of the exposure device 100 can be measured with good precision when an image is captured using diffracted light generated from the surface of the wafer, because variations in the thickness of the resist film or the like make less impact. It is particularly preferred that the wavelength of the illuminating light be 248 nm, 313 nm (j line), or other wavelengths in the deep UV region. The state of variation of the dose of the exposure device 100 can be determined using a plurality of diffraction conditions, and, e.g., averaging on the basis of the diffraction conditions, whereby further improvement in precision can be expected. Also, selecting optimal diffraction conditions for each of various target patterns makes it possible to achieve highly sensitive and high-precision measurements.

Figure 25:
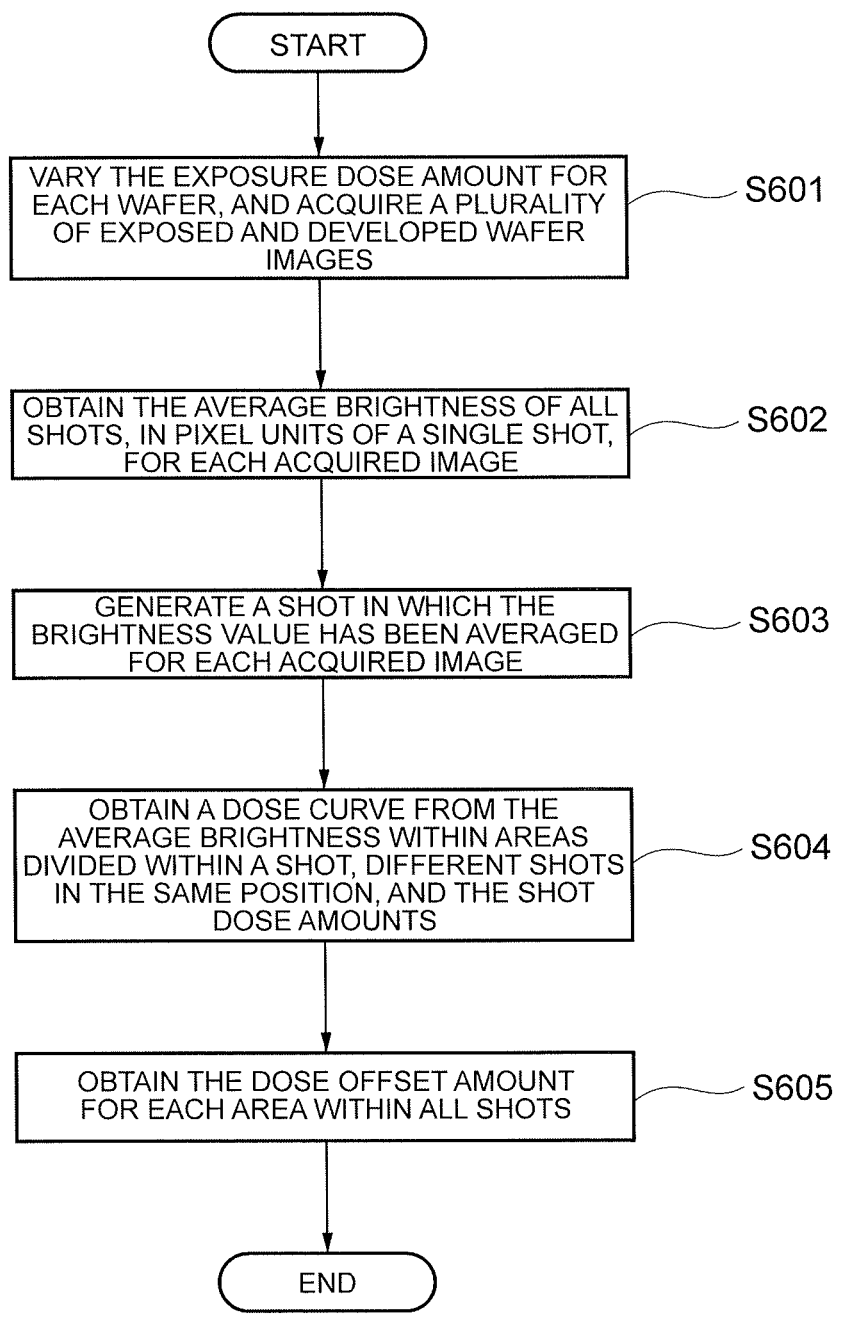
FIG. 25 is a flowchart showing a method for determining the state of variation of the dose in relation to the entire surface of the wafer.

The image processing unit 40 can also determine the state of variation in the dose amount of the exposure device 100 for the entire surface of the wafer 10 using images of a plurality of wafers exposed and developed by varying the dose of the exposure device 100. The method for determining the state of variation in the dose of the exposure device 100 for the surface of the wafer 10 will be described with reference to the flowchart in FIG. 25. First, images of a plurality of wafers (eight wafers having the dose amounts of 10.0 mJ, 11.5 mJ, 13.0 mJ, 14.5 mJ, 16.0 mJ, 17.5 mJ, 19.0 mJ, and 20.5 mJ) exposed and developed by varying the dose amount of the exposure device 100 for each wafer are acquired (step S601). At this point, illumination, imaging, and the like of the wafer are carried out in the same manner as diffraction inspection (conditions in which a predetermined signal intensity is obtained from the pattern exposed and developed under optimal dose amount and optimal focus conditions). As used herein, a plurality of wafers having different dose amounts shall be referred to as measurement wafers.

Next, the average value for all shots within a wafer is determined from the acquired images of the wafers in pixel units of a single shot (or a small area formed by a small number of pixels, and the same applies hereinbelow) for each measurement wafer in which the dose amount of the exposure device 100 has been varied (step S602). Shots in which the brightness value has been substituted by average brightness are subsequently generated for each of the measurement wafers (step S603). A graph, i.e., a dose curve (referred to as a sample dose curve, as appropriate, hereinbelow in order to distinguish from the dose curve that serves as a reference determined using a condition-varied wafer)

showing the relationship between the average brightness (signal intensity) in the set areas in the same position in each shot (having mutually different dose amounts) and the dose amount corresponding thereto is determined for each set area of the shots thus generated (step S604). The approximate curve which approximates the sample dose curve using a function is determined for each of the set areas, and a fourth-order function (a quartic equation) is preferably used as the function of the approximate curve. At this point, the dose offset amount of the exposure device 100 is varied for each of the measurement wafers. Therefore, the dose amount can be determined from the measurement that corresponds to a shot having the generated average brightness, and the average brightness varies in accordance with the dose amount in the set area in the same position within the shot.

Next, the offset amount of the dose that corresponds to the sample dose curve of each set area is determined for the set areas of all the shots using the sample dose curve thus determined (step S605). Specifically, first, fitting (so-called pattern matching) is carried out so that as to optimize the correlation between the sample dose curve of each set area and the reference dose curve of the corresponding set area, which are stored in memory (not shown). At this point, the movement distance of the dose amount in the increase/decrease direction is, in other words, the dose offset amount of the set area.

Using such a configuration makes it possible to determine the state of variation in the dose of the exposure device 100 for the entire surface of the wafer 10 because the distribution of the amount of displacement in the dose on the wafer surface can be determined.

In the present embodiment, a technique for determined the variation in dose was described using the same method as diffraction inspection, but it is also possible to determine the variation in dose by the same method as polarized-light inspection (PER inspection).

In the embodiment described above, it is preferred that a quartic equation be used as the formula of the approximate curve of the dose curve, but it is also possible to perform linear approximation depending on the shape of the graph.

In the embodiment described above, when the state of variation of the dose of the exposure device 100 for the entire surface of the wafer 10 is to be determined, a reference dose curve can be determined in advance for each different focus offset amount, and the reference dose curve may be selected in accordance with the state of variation of the focus in the case that the sensitivity of the signal intensity readily varies in relation to changes in dose due to variation in the focus.

In this manner, in accordance with the embodiments, the focus state during exposure and the dose state can be measured with good precision in a short period of time. Providing the measured focus state and dose state as feedback to the exposure device 100 makes it possible to achieve a line width of an exposed and developed pattern that conforms to design values for the entire surface of the wafer.

In the embodiments described above, the state of focus (focus state) and the exposure amount (dose state) were described as exposure states to be measured, but no limitation is imposed thereby, and it is also possible to apply the technique to the scan speed of the reticle stage and the wafer stage during scan exposure. Also, the exposure state to be measured broadly includes the state of the pattern, and the etching state after development may also be included in the exposure state.

The high performance of an exposure device can be maintained by the present invention, and the occurrence of defects (flaws) can be very considerably reduced even with patterns having very fine line widths. Accordingly, a high-performance semiconductor device can be manufactured without defects in an exposure system having an exposure device in which the present invention has been applied.

Figure 26:
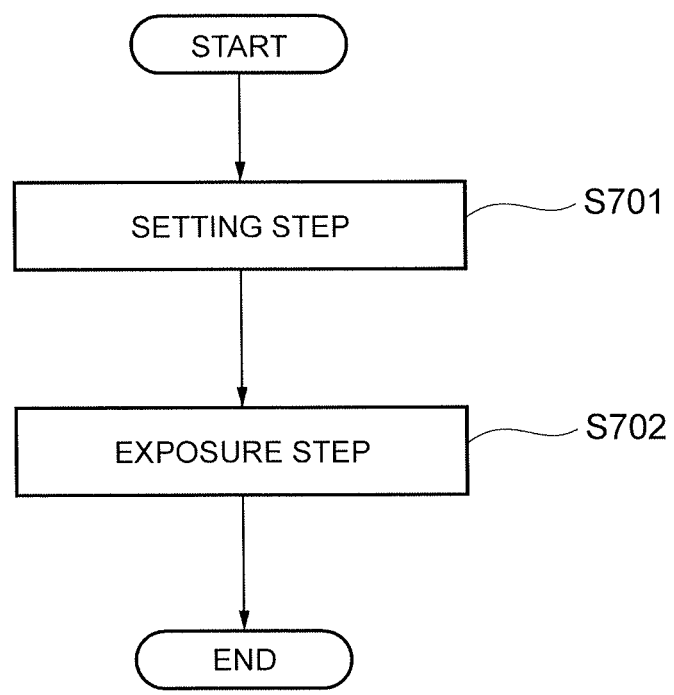
FIG. 26 is a flowchart showing the exposure method.

For example, as shown in FIG. 26, in an exposure method having: a setting step S701 for setting the exposure conditions of the exposure device 100 (settings for each pattern or feedback settings); and an exposure step S702 in which the exposure device 100 performs exposure depending on the exposure conditions thus set, deciding the exposure conditions on the basis of information (the various parameters described above) sent from the signal output unit 90 of the surface inspection device 1 to the exposure device 100 in the setting step S701 makes it possible to maintain the high performance of the exposure device 100. Accordingly, the occurrence of defects (flaws) can be very considerably reduced even with patterns having very fine line widths.

Figure 27:
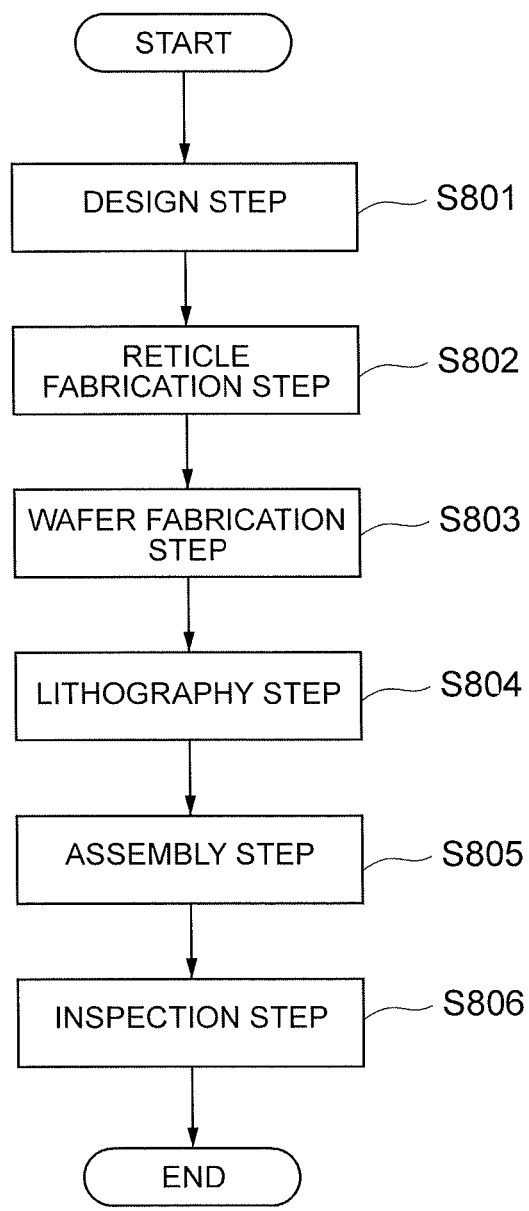
FIG. 27 is a flow chart showing the method for manufacturing a semiconductor device.

As shown in FIG. 27, the semiconductor device (not shown) is manufactured via a design step for designing the functions and performance of a device (step S801), a reticle manufacturing step for manufacturing a reticle on the basis of the design step (step S802), wafer manufacturing step for manufacturing a wafer from silicon material (step S803), a lithography step (including an exposure step, a development step, and/or other steps) for transferring the pattern of the reticle to the wafer by exposure or the like (step S804), an assembly step (including a dicing step, a bonding step, a packaging step, and/or other steps) for assembling the device (step S805), an inspection step for inspecting the device (step S806), and other steps. In the lithography step of such a method for manufacturing a semiconductor device, the pattern is exposed using the exposure method described above, whereby a high-performance semiconductor device can be manufactured without defects because the occurrence of defects (flaws) can be very considerably reduced even with patterns having very fine line widths.

In accordance with the present invention, it is possible to obtain a surface inspection apparatus comprising: a stage for supporting a semiconductor substrate in which a predetermined mask pattern has been projected and exposed by an exposure device to form a semiconductor pattern based on the mask pattern; an illumination unit for irradiating illuminating light onto the surface of the semiconductor substrate supported by the stage; a detection unit for detecting light from the surface of the semiconductor substrate irradiated with illuminating light; a computation unit for determining the tendency of focus displacement within the pattern thus formed, on the basis of information about the light from the surface of the semiconductor substrate detected by the detection unit. The computation unit can determine the tendency in focus displacement on the basis of information about the light from the surface of the projected and exposed semiconductor substrate in which the focus conditions of the exposure device have been varied for each shot. Also, the computation unit detects brightness in each set areas, a plurality of set areas being set in every shot, and find focus conditions in a shot in which the brightness is maximum in each set area. Then the computation unit determines the tendency in focus displacement based on the focus conditions determined in each set area in which the brightness is maximum. It is also possible to furthermore comprise a signal output unit for converting the tendency in focus displacement determined by the computation unit into a signal that can be input to the exposure device, and then outputting the signal to the exposure device. The illumination unit can illuminate the entire surface of the semiconductor substrate on which the patterns have been formed, in a lump using substantially parallel luminous flux, and the detection unit can detect light from the entire surface of the semiconductor substrate in a lump. The illumination unit can irradiate illuminating light onto the surface of the semiconductor substrate so that diffracted light is occurred on the semiconductor pattern of the semiconductor substrate, and the detection unit can detect the diffracted light occurred on the semiconductor pattern of the semiconductor substrate when illuminating light is irradiated. It is also possible to vary the diffraction conditions where the diffracted light is occurred, to have the illumination unit irradiating illuminating light onto the surface of the semiconductor substrate, to have the detection unit detecting the diffracted light that corresponds to the diffraction conditions, and to have the computation unit determining the tendency in focus displacement on the basis of information about the diffracted light detected in a plurality of diffraction conditions. The illumination unit can irradiate substantially linearly polarized light as illuminating light onto the surface of the semiconductor substrate, and the detection unit can detect changes in the polarized light produced by structural birefringence in the semiconductor pattern of the semiconductor substrate irradiated by polarized light.

It is also possible to obtain an inspection apparatus comprising: a stage for supporting a semiconductor substrate in which a semiconductor pattern has been exposed and formed by an exposure device on the surface of the substrate; an illumination unit for irradiating illuminating light onto the surface of the semiconductor substrate supported by the stage; a detection unit for detecting light from the surface of the semiconductor substrate irradiated with illuminating light; a computation unit for determining the state of variation in focus of the exposure device for the surface of the semiconductor substrate, on the basis of information about the light from the surface of the semiconductor substrate detected by the detection unit. It is also possible to furthermore comprise a storage unit for storing the relationship between the state of variation of focus of the exposure device and the light from the surface of the semiconductor substrate, and the computation unit can determine the state of variation in focus of the exposure device on the basis of the information stored in the storage unit and the light from the surface of the semiconductor substrate to be inspected. The illumination unit can irradiate illuminating light onto the surface of the semiconductor substrate so that diffracted light is occurred on the semiconductor pattern of the semiconductor substrate, and the detection unit can detect diffracted light occurred on the semiconductor pattern of the semiconductor substrate irradiated by the illuminating light. The illumination unit can irradiate substantially linearly polarized light as illuminating light onto the surface of the semiconductor substrate, and the detection unit can detect changes in the polarized light produced by structural birefringence in the semiconductor pattern of the semiconductor substrate irradiated by polarized light. The illumination unit can irradiate illuminating light onto the surface of the semiconductor substrate so that diffracted light is occurred on the semiconductor pattern of the semiconductor substrate, the detection unit can detect the diffracted light occurred on the semiconductor pattern of the semiconductor substrate when illuminating light is irradiated. The illumination unit can irradiate substantially linearly polarized light as illuminating light onto the surface of the semiconductor substrate, and the detection unit can detect changes in the polarized light produced by structural birefringence in the semiconductor pattern of the semiconductor substrate irradiated by polarized light. The computation unit can determine state of variation in focus of the exposure device on the basis of information about the diffracted light detected by the detection unit and information about change in the polarized light detected by the detection unit.

EXPLANATION OF NUMERALS AND CHARACTERS

1: surface inspection apparatus
5: stage (modification unit)
10: wafer (10a condition-varied wafer)
15a to 15e: measurement wafer
20: illumination system (illumination unit)
30: light-receiving system
35: imaging device (detection unit)
40: image processing unit (computation unit)
60: inspection unit
80: controller
82: communication port (input unit)
85: storage unit
90: signal output unit
100: exposure device

The invention claimed is:
1. An inspection apparatus comprising:
an illumination unit for irradiating an illuminating light on a plurality of patterns which are formed on a substrate together or on a plurality of substrates separately, which were made by exposure, the patterns comprising a first set of patterns and a second set of patterns, wherein the first set of patterns and the second set of patterns are irradiated separately or together;
a detection unit for detecting light from the patterns on which the illuminating light has been irradiated;
a computation unit for determining an exposure state of an exposure device when the patterns were made, the exposure state comprising an exposure amount and a focus state, wherein:
    the computation unit:
        determines a first relationship between:
            a plurality of different exposure states and detected results of the light from the first set of patterns made under the plurality of different exposure states,
        determines a second relationship between:
            a plurality of different exposure states and detected results of the light from the second set of patterns made under the plurality of different exposure states,
        compares the exposure states and detected results of the first relationship and the exposure states and detected results of the second relationship; and
        determines the exposure state of the exposure device in effect when the first set of patterns or the second set of patterns were exposed, on the basis of a result compared between the exposure states and detected results of the first relationship and the exposure states and detected results of the second relationship; and
an output unit for outputting the exposure state determined by the computation unit to at least one of the exposure device and a computer which is communicably connected to the exposure device, wherein
    the computer outputs the exposure state determined by the computation unit to the exposure device to set the exposure state of the exposure device, the focus state of the exposure device is determined by setting, based on the exposure state determined by the computation unit, a relative location between a pattern image to be exposed and a substrate, and the exposure amount is determined by setting, based on the exposure state determined by the computation unit, an exposure light intensity or an exposure time period.

2. The inspection apparatus according to claim 1, wherein the computation unit computes as the exposure state at least one of an exposure amount and a focus state in effect when the patterns were exposed.

3. The inspection apparatus according to claim 2, further comprising
a controller for controlling the illumination unit and the detection unit, the controller controlling at least one of the illumination unit and the detection unit so that:
a change of at least one of the first and second relationships due to an offset of the focus state in effect is smaller than that due to an offset of the exposure amount; or
a change of at least one of the first and second relationships due to an offset of the exposure amount is smaller than that due to an offset of the focus state in effect.

4. The inspection apparatus according to claim 1, 2, or 3, wherein the detection unit detects diffracted light from the patterns.

5. The inspection apparatus according to claim 4, wherein the detection unit detects diffracted light of a fourth order or greater.

6. The inspection apparatus according to claim 1, 2, or 3, wherein the detection unit detects a predetermined polarized light component in light reflected from the patterns.

7. The inspection apparatus according to claim 1, wherein the detection unit detects light from the patterns over a plurality of times, and the computation unit determines the exposure state on the basis of an integral signal obtained by integrating the results of the plurality of detections.

8. The inspection apparatus according to claim 1, wherein the illumination unit illuminates in a lump, using substantially collimated light, an entire surface on which the plurality of patterns were formed; and
the detection unit detects in a lump the light from the plurality of patterns on the surface.

9. The inspection apparatus according to claim 1, further comprising an output unit for outputting the exposure state determined by the computation unit, the exposure state being sent so as to be capable of being fed back to an exposure device that performed the exposure.

10. An inspection method comprising the steps of:
irradiating an illuminating light on a plurality of patterns which are formed on a substrate together or on a plurality of substrates separately, which were made by exposure, the patterns comprising a first set of patterns and a second set of patterns, wherein the first set of patterns and the second set of patterns are irradiated separately or together;
detecting light from the patterns on which the illuminating light has been irradiated; and
determining an exposure state of an exposure device when the patterns were made, the exposure state comprising an exposure amount and a focus state, wherein the determining step comprises:
determining a first relationship between:
a plurality of different exposure states; and
detected results of the light from the first set of patterns made under the plurality of different exposure states,
determining a second relationship between:
a plurality of different exposure states; and
detected results of the light from the second set of patterns made under the plurality of different exposure states;
comparing the exposure states and detected results of the first relationship and the exposure states and detected results of the second relationship;
determining the exposure state of the exposure device in effect when the plurality of patterns were exposed, on the basis of a result compared between the exposure states and detected results of the first relationship and the exposure states and detected results of the second relationship; and
outputting the determined exposure state to at least one of the exposure device and a computer which is communicably connected to the exposure device, wherein
the computer outputs the exposure state determined by the computation unit to the exposure device to set the exposure state of the exposure device,
the focus state of the exposure device is determined by setting, based on the exposure state determined by the computation unit, a relative location between a pattern image to be exposed and a substrate, and
the exposure amount is determined by setting, based on the exposure state determined by the computation unit, an exposure light intensity or an exposure time period.

11. The inspection method according to claim 10, wherein at least one of an exposure amount and a focus state in effect when the patterns were exposed is determined as the exposure state.

12. The inspection method according to claim 11, wherein at least one of an illumination unit configured to illuminate and a detection unit configured to detect results are controlled so that a change of at least one of the first and second relationships due to an offset of the focus state in effect is smaller than that due to an offset of the exposure amount, or a change of at least one of the first and second relationships due to an offset of the exposure amount is smaller than that due to an offset of the focus state in effect.

13. The inspection method according to claim 10, 11, or 12, wherein diffracted light from the patterns is detected.

14. The inspection method according to claim 10, 11, or 12, wherein a predetermined polarized light component of light from the patterns is detected.

15. The inspection method according to claim 10, wherein light from the patterns is detected over a plurality of times, and the exposure state is determined on the basis of an integral signal obtained by integrating the results of the plurality of detections.

16. The inspection method according to claim 10, wherein an entire surface on which the patterns were formed is illuminated in a lump, and the light from the patterns on the entire surface is detected in a lump.

17. The inspection apparatus according to claim 1, wherein the computation unit determines the exposure state when the second set of patterns were made based on the comparison.

18. The inspection apparatus according to claim 1, wherein the first and second relationships are respectively represented by first and second functions, and the comparison is made by comparing the functions.

19. The inspection apparatus according to claim 18, wherein the comparison is made by determining the correlation in shifting the first function to or from the second function.

20. The inspection apparatus according to claim 18, wherein the comparison of the functions is made at the exposure state when the detected result by the detection unit becomes maximum.

21. The inspection apparatus according to claim 18, 19, or 20, wherein the functions are polynomials of a fourth order or higher.

22. The inspection method according to claim 13, wherein diffracted light of a fourth order or greater is detected.

23. The inspection method according to claim 10, wherein the exposure state is determined when the second set of patterns were made based on the comparison.

24. The inspection method according to claim 10, wherein the first and second relationships are respectively represented by first and second functions, and the comparison is made by comparing the functions.

25. The inspection method according to claim 24, wherein the comparison is made by determining the correlation in shifting the first function to or from the second function.

26. The inspection method according to claim 24, wherein the comparison of the functions is made at the exposure state when the detected result becomes maximum.

27. The inspection method according to claim 24, 25, or 26, wherein the functions are polynomials of a fourth order or higher.

28. The inspection apparatus according to claim 1, wherein the plurality of patterns are on a substrate.

29. The inspection apparatus according to claim 28, further comprising
a modification unit for modifying at least one of the relative position between the substrate and the detection unit and the relative position between the substrate and the illumination unit, wherein:
the detection unit detects results of light from the plurality of patterns before and after modification of the relative position; and
the computation unit determines the exposure state when the second set of patterns were exposed, on the basis of the detected results before and after modification of the relative position.

30. The inspection apparatus according to claim 29, wherein the computation unit determines the exposure state on the basis of the average of the detected results for a plurality of the relative positions.

31. The inspection method according to claim 10, wherein the plurality of patterns are on a substrate.

32. The inspection method according to claim 31, further comprising:
modifying at least one of the relative position between the substrate and a detection unit configured to detect results and the relative position between the substrate and an illumination unit configured to illuminate,
detecting results of light from the plurality of patterns before and after modification of the relative position by the detection unit; and
determining the exposure state when the second set of patterns were exposed on the basis of the detected results produced before and after modification of the relative position.

33. The inspection method according to claim 32, wherein the exposure state is determined on the basis of the average of the detected results produced for a plurality of the relative positions.

* * * * *